(12) United States Patent
Duvvuri et al.

(10) Patent No.: US 6,177,439 B1
(45) Date of Patent: Jan. 23, 2001

(54) WATER SOLUBLE ANALOGUES OF 20(S)-CAMPTOTHECIN

(75) Inventors: Subrahmanyam Duvvuri; Venkateswarlu Akella; Sharma Manohara Vedula; Sastry V. R. S. Thungathurthi; Vamsee Krishna Chintakunta; Shobha Madabhushi, all of Andhra Pradesh (IN)

(73) Assignees: Reddy's Research Foundation, Hyderabad, IN (US); Reddy-Cheminor, Inc., Ridgewood, NJ (US)

( * ) Notice: Under 35 U.S.C. 154(b), the term of this patent shall be extended for 0 days.

(21) Appl. No.: 08/771,391

(22) Filed: Dec. 19, 1996

Related U.S. Application Data

(63) Continuation-in-part of application No. 08/655,259, filed on Jun. 5, 1996, now abandoned, which is a continuation-in-part of application No. 08/471,640, filed on Jun. 6, 1995, now abandoned.

(51) Int. Cl.[7] .................. A61K 3/4745; C07D 491/22

(52) U.S. Cl. .................................. 514/283; 546/48

(58) Field of Search ....................... 546/48; 514/283

(56) References Cited

U.S. PATENT DOCUMENTS

| | | | |
|---|---|---|---|
| 4,399,282 | 8/1983 | Miyasaka | 546/48 |
| 4,473,692 | 9/1984 | Miyasaka | 546/48 |
| 4,513,138 | 4/1985 | Miyasaka | 546/48 |
| 4,545,880 | 10/1985 | Miyasaka | 204/158 |
| 4,604,463 | 8/1986 | Miyasaka | 546/48 |
| 4,981,968 | 1/1991 | Wall | 544/361 |
| 5,053,512 | 10/1991 | Wani | 546/48 |
| 5,122,526 | 6/1992 | Wall | 514/253 |
| 5,391,745 | 2/1995 | Danishefsky | 546/48 |
| 5,446,047 | 8/1995 | Danishefsky | 514/280 |
| 5,468,754 | 11/1995 | Hausheer | 514/283 |
| 5,525,731 | 6/1996 | Danishefsky | 546/48 |
| 5,541,237 * | 7/1996 | Donishefsky et al. | 546/48 |

FOREIGN PATENT DOCUMENTS

| | | |
|---|---|---|
| 0074256 | 3/1983 | (EP) . |
| 2056973 | 3/1981 | (GB) . |
| 58-39683 | 3/1983 | (JP) . |
| 58-39684 | 3/1983 | (JP) . |
| 58-154584 | 9/1983 | (JP) . |
| 58-15483 | 9/1983 | (JP) . |
| 58-15484 | 9/1983 | (JP) . |
| 97/46563 * | 12/1997 | (WO) . |

OTHER PUBLICATIONS

Seigo Sawada, "Synthesis and Anitumor Activity of 20(S), Camptothecin Derivatives:Carbamate–Linked, Water–Soluble, Derivatives of 7–Ethyl–10–hydroxycamptothecin", Chem. & Pharm. Bulletin, Japan, vol. 39, No. 6, pp. 1446–1454 (1991).*

Lawrence Snyder, "Synthesis of 19–Noranhydrocamptothecin Analogs Which Retain Topoisomerase I Inhibitory Function" J. Org. Chem 1994, 59, 7033–7037.*

(List continued on next page.)

Primary Examiner—Bruck Kifle
(74) Attorney, Agent, or Firm—Ladas & Parry

(57) ABSTRACT

Novel water soluble C-ring analogues of 20(S)-camptothecin having the general formula 1,

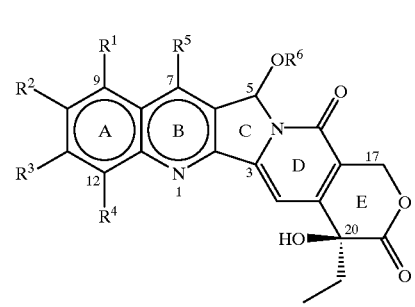

All the compounds of the formula 1 are prepared from the compounds of the general formula 2 having 20(S)-chiral carbon where $R^1$ to $R^5$ have the meaning given above. The compounds of the formula 1 possess potent anti-cancer and anti-viral properties.

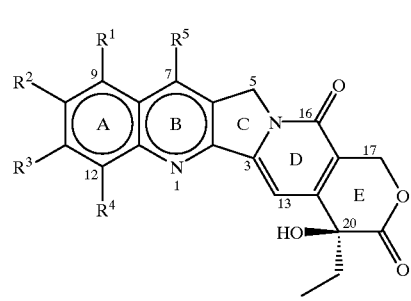

The invention also provides an alternate process for the preparation of known C-5 substituted compounds of the formula 1,

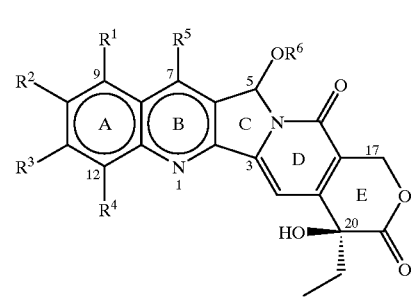

31 Claims, No Drawings

OTHER PUBLICATIONS

Akio Ejima, "Antitumor Agents V. Synthesis and Antileukemic Activity of E–Ring–Modified (RS)–Camptothecin Analogues" Chem. Pharm. Bull. 40(3), 683–688, Mar. 1992.*

Takashi Yaegashi, "Chemical Modification of Antitumor Alkaloids, 20(S)–Camptothecin and 7–Ethylcamptothecin: Reaction of the E–Lactone Ring Portion with Hydrazine Hydrate", Chem. Pharm. Bull. 41(5) 971–974 (1993).*

Mansukh C. Wani, "Plant Antitumor Agents.23.[1] Synthesis and Antileukemic Activity of Camptothecin Analogues", J. Med. Chem., 1986, 29, 2358–2363.*

Robert P. Hertzberg, "Modification of the Hydroxy Lactone Ring of Camptothecin: Inhibition of Mammalian Topoisomerase I and Biological Activity", J. Med. Chem. 1989, 32, 715–720.*

Yaw–Huei Hsiang, "Camptothecin Induces Protein–linked DNA Breaks via Mammalian DNA Topoisomerase I", Journal of Biological Chemistry, vol. 260, No. 27,p. 14873–14888 (1986).*

Monroe E. Wall, "Plant Antitumor Agents 30 Synthesis and Structure Activity of Novel Camptothecin Analogs" J. Med. Chem. 1993, 2689–2700.*

Thomas G. Burke, "The Structural Basis of Camptothecin Interactions with Human Serum Albumin: Impact on Drug Stability" J. Med. Chem. 1994, 37, 40–46.*

Lokiec et al. (Clin. Cancer Res (1996), 2(12), 1943–1949), 1996.*

Cao, J. Chem Soc. Perkin Trans. I 1996 pp 2629–32, 1996.*

T. R. Govindachari, "9–Methoxycamptothecin. A New Alkaloid fromMappia foetida Miers", Indian J. Chem. vol. 10, 453–454 (1972).*

Zhuo–Feng Xie, "Convergent Approach to Water Soluble Camptothecin Derivatives", Bioorganic & Medicinal Chemistry Letters, vol. 5, No. 19, pp. 2189–2194, 1995.*

English Translation JP–A–58–154584 (Yakurt Co. Ltd).*

Heterocycles, vol. 38, No. 1, 1994 p. 81–94, Sugimori, et al.*

Bioorganic & Medicinal Chemistry Letters. vol. 5. No. 1 pp. 77–82, 1995, Wang et al.*

Chem. Pharm. Bull., vol. 39, 3183 (1991), Sawada et al.*

J. Org. Chem., vol. 60, 5739–5740 (1995), Wood et al.*

Chem. Pharm. Bull., 41 (2), 310–313 (1993), Yaegashi et al.*

Chem. Pharm. Bull., 39, No. 10 pp. 2574–2580 (1991), S. Sawada et al.*

J. Med. Chem., 34, 98–107 (1991), W.D. Kingsbury et al.*

Cancer Research., 49, 5016 (1989), Covey et al.*

Cancer Research., 51, 3052 (1991), Giovanella, et al.*

Biochemistry., 33, 12540 (1994), Mi et al.*

Chemical Abstracts, vol. 100, 1984, p. 604 Abstract 51876f.*

Biochemical Pharmacology, vol. 34, No. 8, Apr. 15, 1985, Masako Fukada, et al. P. 1225–1230.*

Database WPI–AN92–71412EXP002034966 JP 57116074A (Yakult Honska K.K.) Jul. 19, 1982.*

Chemical Abstracts vol. 100, No. 11, Mar. 12, 1984, Abstract No. 85671a JP 58–154 583A (Yakult Co.).*

Chemical Abstracts vol. 100, No. 7, Feb. 13, 1984, Abstract No. 51876f JP 58 154 584A (Yakult Co.).*

* cited by examiner

WATER SOLUBLE ANALOGUES OF 20(S)-CAMPTOTHECIN

This application is a continuation-in-part of application Ser. No. 08/655,259 filed on Jun. 5, 1996 now abandoned which is a CIP of Ser. No. 08/471,640 filed Jun. 6, 1995 now abandoned.

The present invention relates to novel water soluble C-ring analogues of 20(S)-Camptothecin having the general formula 1.

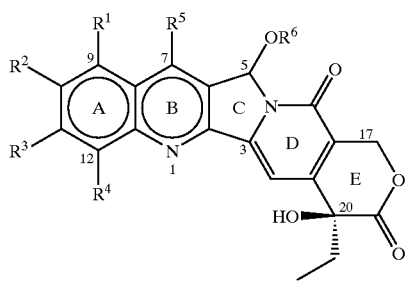

1

In the above formula 1, $R^1$, $R^2$, $R^3$, $R^4$ are independently the same or different and represent hydrogen, hydroxy, aryloxy, lower alkoxy, lower alkanoyl, nitro, cyano, halo, carboxy, carbonyloxy, amino, substituted amino, lower alkyl, substituted lower alkyl, or $R^2$, $R^3$ together represent —O—$(CH_2)_n$—O— where n=1 or 2; $R^5$ represents hydrogen, lower alkyl, substituted lower alkyl, lower aralkyl, hydroxymethyl, carboxymethyl, aminomethyl, substituted aminomethyl where the amino group may be mono or disubstituted in which both substituents are independent or combined together to form a cyclic ring system of a total of 5–6 atoms containing carbon and optionally one or two heteroatoms selected from oxygen, nitrogen or sulfur; and $R^6$ represents hydrogen, phenyl or benzyl where the phenyl group may be unsubstituted or substituted with mono, di or trisubstituents which may be selected from halogen, hydroxy, lower alkoxy, cyano, carboxyl, nitro, amino or substituted amino, lower alkyl, substituted lower alkyl; cycloalkyl or cycloalkyl lower alkyl where the cyclic ring is in the range of 3 membered to 7 membered ring system containing all carbon atoms; lower alkyl groups substituted with heterocyclic rings where the heterocyclic ring system has a total of 3 to 7 atoms, the heterocyclic rings containing carbon with at least one heteroatom such as oxygen, nitrogen or sulfur; lower alkanoyl; benzoyl where the phenyl group can be unsubstituted or substituted; lower alkenyl; lower alkyl; substituted lower alkyl, substituted lower alkenyl or substituted lower alkanoyl where the substituents can be halogen, hydroxy, lower alkoxy, aryloxy, thio, thioalkyl, thioaryl, aryl, heteroaryl, carboxy, cyano, nitro, amido or amino in which the amino group can be unsubstituted or mono, or disubstituted in which both substituents are independent or combined together to form 5 or 6 membered cyclic ring system containing carbon, and optionally contain one or two heteroatoms selected from oxygen, nitrogen or sulfur, the total number of atoms in the cyclic ring system is 5 or 6; with the proviso that (i) when $R^1$ is methoxy group, $R^6$ is not hydrogen or lower alkyl group; (ii) when $R^2$ is hydroxy, lower alkoxy, thioalkyl, nitro, amino, alkylamino, acylamino or halogen, $R^6$ is not hydrogen or lower alkyl group; (iii) when $R^5$ is lower alkyl, lower aralkyl, $CH_2OH$, COOH, COOMe or $CH_2OR''$ where $R''$ represents lower alkyl or acyl group, $R^6$ is not hydrogen or lower alkyl group; (iv) when $R^1$ is methoxy group, $R^2$ is hydroxy, lower alkoxy, thioalkyl, nitro, amino, alkylamino, acylamino, or halogen, $R^5$ is lower alkyl, lower aralkyl, $CH_2OH$, COOH, COOMe or $CH_2OR''$ where $R''$ represents lower alkyl or acyl group, $R^6$ is not hydrogen or lower alkyl group; (v) when $R^1$ through $R^5$ represent hydrogen, $R^6$ is not hydrogen or lower alkyl group.

All these compounds of the formula 1 are prepared from the compounds of the general formula 2 having 20(S)-chiral center,

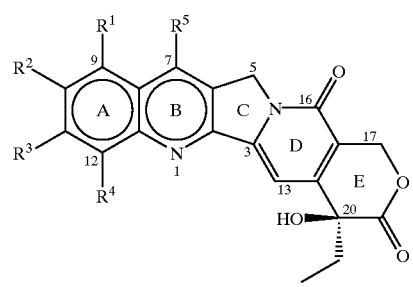

2 where $R^1$ to $R^5$ have the meaning described above. Camptothecin having the formula 3, is an alkaloid with strong antitumor activity,

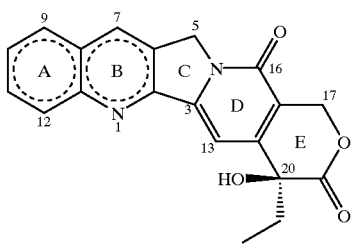

3 and was isolated from *Camptotheca acuminata* by Wall and co-workers in 1966. However, its development as a potential drug for cancer treatment had been abandoned due to unacceptable side effects on humans and due to its low water solubility as well as high toxicity problems. Since the discovery of its mechanism of action as an inhibitor of topoisomerise I by Liu and co-workers in 1985 [L. F. Liu, et al., *J. Biol. Chem.*, 260, 14873 (1985)], the research interest on camptothecin has once again taken momentum.

To overcome this problem of low water solubility and high toxicity of camptothecin, over the last 30 years, several research groups all over the world have prepared and investigated a number of camptothecin analogues involving the modification of rings A–E or the introduction of a variety of substituents on all the five rings of camptothecin of the formula 3 [M. E. Wall et al., *J. Med. Chem.*, 36, 2689 (1993); R. P. Hertzberg et al., *J. Med. Chem.*, 715 (1989); S. W. Sawada et al., *Chem. Pharm. Bull.*, 41(2), 310 (1993)]. Among the various camptothecin analogues prepared to date, only two of them namely, CPT-11 having the formula 4 [*Chem. Pharm. Bull.*, 39, 1446 (1991)],

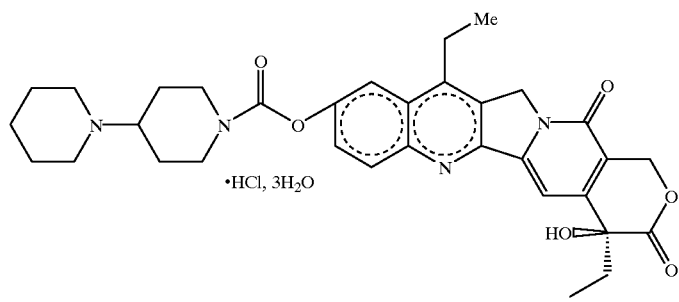

4 topotecan of the formula 5 [*J. Med. Chem.*, 34, 98(1991)]

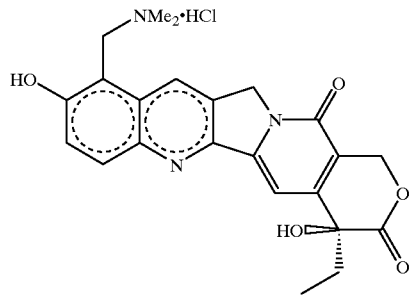

5 were introduced as anti-cancer drugs in the market recently. Another compound namely, 9-aminocamptothecin of the formula 6 [*J. Med. Chem.*, 29, 2358 (1986)],

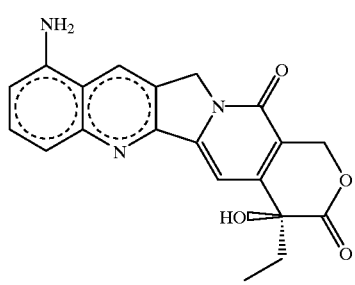

6 is currently undergoing extensive clinical trials. The extensively studied Structure Activity Relationship (SAR) on camptothecin of the formula 3 [M. E. Wall et al., *J. Med. Chem.*, 36, 2689 (1993)] has revealed that 20(S)-α-hydroxy-δ-lactone (E-ring) moiety in camptothecin is essential for its activity. However, according to recent reports by Ejima et al., replacement of hydroxyl group with an amino group at C-20 position leading to a compound such as 7-ethyl-10-methoxycamptothecin derivative of the formula 7 [A. Ejima et al., *Chem. Pharm. Bull.*, 40(3), 683 (1992)],

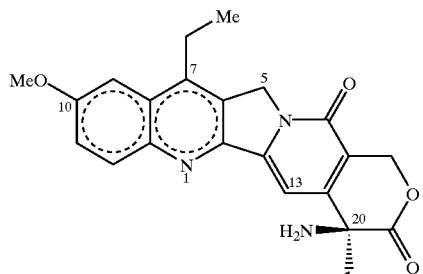

7

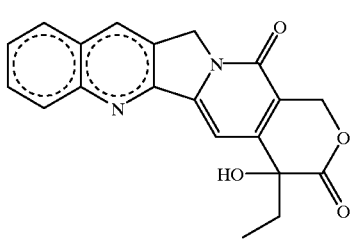

8 exhibited an increased in vivo antitumor activity than 20(RS)-camptothecin of the formula 8. Also in another report (Lawrence Snyder et al., *J. Org. Chem.*, 59, 7033 (1994)], the 18-noranhydrocamptothecin analogue of the formula 9,

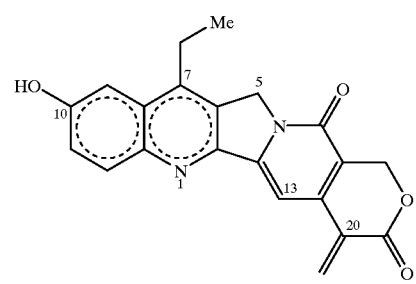

9 exhibited potent camptothecin like inhibition of topoisomerase I activity. Both these reports are contrary to the assumption that 20(S)-α-hydroxy functionality in camptothecin is an essential feature for its biological activity.

Based on the structure-activity results obtained for the camptothecin analogues prepared in the literature, it was established that the modification of substituents at C-9 and C-7 position of camptothecin of the formula 3 plays an important role in the enhancement of anticancer activity by imparting stability to the E-ring lactone [T. G. Burke et al., *J. Med. Chem.* 37, 40 (1994)]. It has also been recognized that the open form of the lactone moiety, namely, 'the Carboxylate form' is less effective therapeutically than the closed 'Lactone form' [Hertzberg et al., *J. Med. Chem.,* 32, 715(1989); J. M. Covey, C. Jaxel et al., *Cancer Research.,* 49, 5016 (1989); Giovanella et al., *Cancer Research.,* 51, 3052 (1991)]. The recent studies by T. G. Burke et al., on the stability of 'closed lactone form' of various camptothecin analogues in the presence of protein called 'Human Serum Albumin' (HSA) indicated that the compounds such as CPT-11 of the formula 4 and 7-ethyl-10-hydroxycamptothecin (SN-38) of the formula 7a

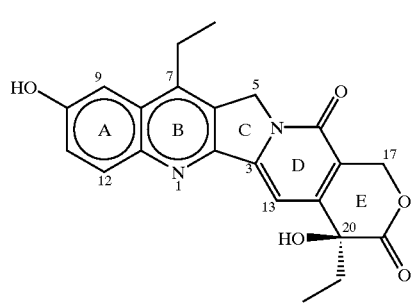

7a and Topotecan of the formula 5, in the presence of HSA at 37° C., exhibited a higher percentage (%) of lactone form at equilibrium than 20(S) camptothecin of the formula 3 and 9-aminocamptothecin of the formula 6 [T. G. Burke and Zihou Mi., *J. Med. Chem.,* 37, 40 (1994); ibid., *Biochemistry.,* 33, 12540 (1994)]. Based on these studies, it was recognized that the understanding of the factors influencing the lactone-carboxylate equilibrium of camptothecin analogues became an important determinant in the design of novel and therapeutically efficacious drug candidates in the camptothecin series.

Although the modification of substituents on rings A and B of camptothecin was taken up at a rapid pace to generate novel CPT analogues, ring 'C' analogues of camptothecins were limited presumably because of the research work carried out by Sawada et al., which claimed that the substituents at C-5 position of camptothecin has resulted in the reduction of anti-tumor activity of camptothecins and produced inactive analogues [Sawada S. et al., *Chem. Pharm. Bull.,* 39(10), 2574 (1991)]. The C-5 substituted camptothecins claimed by Sawada et al., (JP 58, 154,584; U.S. Pat. No. 4,513,138; U.S. Pat. No. 4,473,692; U.S. Pat. No. 4,545,880; U.S. Pat. No. 4,339,282) have the structural formula 10,

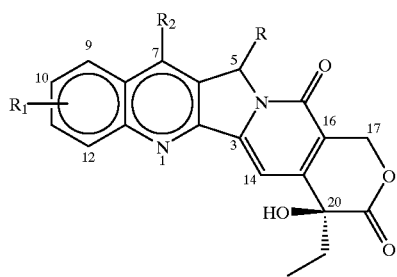

10 where R represents hydroxy, lower alkyl, lower alkoxy, acyloxy groups, $R^1$ represents hydrogen, methoxy at 9th position; hydrogen, hydroxy, lower alkoxy, acyloxy, SH, thioalkyl, thioacyl, nitro, amino, alkylamino, acylamino and halogen groups at 10th position and $R^2$ represents hydrogen, lower alkyl, lower aralkyl, $CH_2OH$, COOH, COOMe, $CH_2OR'$ where R' represents lower alkyl or acyl group.

The recent findings by K. H. Lee et al., [*Bio. Org. Med. Chem. Lett.,* 5(1), 77 (1995)] which includes the preparation of 5-hydroxymethyl camptothecin by the reaction of formaldehyde in N,N-dimethylformamide and 4-piperidinopiperidine on 20(S)-camptothecin, has revealed the reduced anti-tumor activity of these compounds. Also, Danishefsky et al., prepared some of the C-5 substituted 20(RS)-camptothecin derivatives by a totally synthetic approach [U.S. Pat. No. 5,391,745 and U.S. Pat. No. 5,446,047].

However, the synthetically prepared 5-substituted camptothecin derivative of the formula 11 [Terasawa et al., *Heterocycles,* 38, 81 (1994)] claimed to have anti-tumor activity comparable to that of 20(S)-camptothecin.

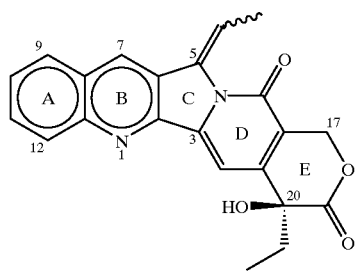

11

Keeping all these factors in mind, we focused our research studies on 20(S)-camptothecin aimed at the design of novel camptothecin analogues which can exhibit improved water solubility and improved stability of lactone form in solution. We identified a oxidative reaction in alcoholic solvents for this purpose. The resultant findings have culminated into the discovery of a novel synthetic transformation which can introduce a variety of alkoxy groups at C-5-position of 20(S)-camptothecins. Functional group transformation of these 5-alkoxy camptothecins produced a wide variety of novel C-5 substituted 20(S)-camptothecin analogues of the formula 14,

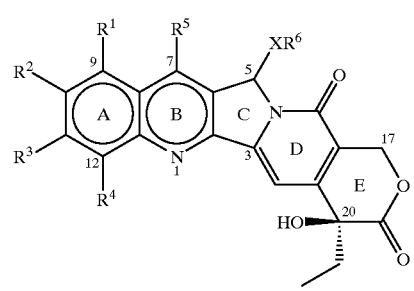

14 in which X represents NH or NR and $CH_2$ or CHR and $R^6$ has the meaning described above, which is the subject matter of our co-pending application for patents bearing U.S. application Ser. No. 08/771,390 and U.S. application Ser. No. 08/772,071.

Hence, the discovery led to a facile and versatile semi-synthetic methodology by which virtually every camptothecin derivative known in the literature can be transformed into a variety of C-5 substituted camptothecin analogues.

Therefore, the present invention provides a novel process for the preparation of various C-5 substituted 20(S)-camptothecin derivatives of the formula where $R^6$ has the meaning described above. Also, by virtue of the present invention, a second chiral center at C-5 position was introduced into the camptothecins of the general formula 2 without disturbing the existing 20-hydroxyl group, C-20(S) chiral center. Furthermore, the vast variety of substituents represented by $OR^6$ at the C-5 carbon of 20(S)-camptothecins of the formula 1 led to compounds with improved water solubility ranging from 1 mg to 10 mg per ml. All of the compounds prepared by the present invention exhibited significant in vitro anti-tumor activity against a wide range of human tumor cell lines.

DETAILED DESCRIPTION OF THE INVENTION

The present invention particularly provides C-5-O-substituted water soluble analogues of 20(S)-Camptothecin having the formula 1,

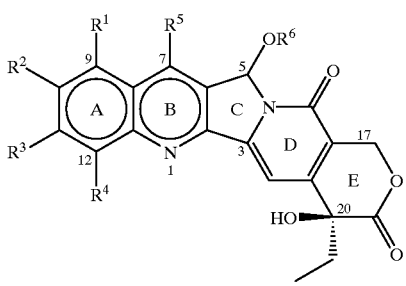

1 where $R^1$, $R^2$, $R^3$, $R^4$, $R^5$ and $R^6$ have the meaning described above. Throughout the present invention, the terms representing $R^1$ through $R^6$ in these compounds have the following definitions.

The term 'lower alkyl' denotes a univalent, branched or straight hydrocarbon chain containing 1 to 8 carbon atoms. Representative of the alkyl groups are methyl, ethyl, propyl, isopropyl, butyl, sec.butyl tert.butyl pentyl, iso pentyl tert.pentyl, hexyl, isohexyl and octyl.

The term 'lower alkenyl' represents a branched or straight hydrocarbon chain having sp or $sp^2$ carbon centers containing 1 to 8 carbon atoms. Representative of the alkenyl groups are vinyl, propenyl, butenyl pentenyl, isopropenyl, isobutenyl, proparginyl, hexenyl and octenyl.

The term 'halogen' or 'halo' represents chlorine, bromine or fluorine. The term 'haloalkyl' denotes alkyl groups substituted with halogens, preferably fluorine, bromine or chlorine. Representative of the haloalkyl groups are chloroethyl, bromopropyl, fluoroethyl, trifluoroethyl, trichloroethyl and trifluorobutyl.

The term 'lower alkoxy' denotes lower alkyl groups as defined above attached via oxygen linkage to the rest of the molecule. Representative of those groups are methoxy, ethoxy, isopropoxy, tert.butoxy, hexoxy, heptoxy and octoxy.

The term 'lower alkanoyl' denotes lower alkyl or alkenyl groups as defined above attached via a carbonyl group to the rest of the molecule. Representative of those groups are acetyl, propionyl, propenoyl, crotanoyl, butanoyl, pentanoyl and isopentanoyl.

The term 'aminoalkyl' represents the lower alkyl groups as defined above substituted with amino groups. Representative of the aminoalkyl groups are 2-aminopropyl, 4-aminobutyl, 5-aminopentyl. Amino groups may also be mono or disubstituted and the representative of these substituted amino groups are dimethylamino, diethylamino, dibenzylamino, ethylisopropylamino, pyrrolidino, piperidino, morphilino or piperizino.

The term 'heteroatom' refers to oxygen, nitrogen or sulfur. The term 'aryl or heteroaryl' represents the groups of aromatic nature having 5 or 6 membered rings which may be selected from phenyl, biphenyl, naphthyl, pyridyl, quinoline, isoquinoline, indole, pyrole, furan, benzofuran, thiophene, pyrimidine, thiosolidine or imidazole.

The term 'substituted phenyl' group used in the present invention refers to those substituents which can be selected from the groups such as hydroxyl, lower alkyl, haloalkyl, phenyl, benzyl, halogen, lower alkoxy, thioalkoxy, benzyloxy, carboxyl, cyano, nitro, amido, amino, and alkylamino. Examples of such groups are 4-hydroxyphenyl, 3-methoxyphenyl, 4-fluorophenyl, 4-trifluoromethylphenyl, N,N-dimethylaminophenyl, and 4- carbomethoxyphenyl.

The term 'substituted alkyl' group used in the present invention refers to those substituents which can be selected from the groups such as hydroxyl, alkyl, haloalkyl, phenyl, benzyl, halogen, alkoxy, thioalkoxy, benzyloxy, carboxyl, carbonyloxy, cyano, nitro, amido, amino, and alkylamino. Examples of such groups are fluoroethyl, chloropropyl, hydroxyethyl, methoxypropyl, N,N-diethylaminoethyl, N-benzoylaminopropyl, trifluoroethoxyethyl, phenoxyethyl, carbomethoxyethyl, (p-fluorobenzoyloxy)ethyl, aminopropyl, and 2-thioethyl.

The term 'substituted amino' group used in the present invention refers to those substituents which can be selected from the groups such as hydroxyl, alkyl, haloalkyl, benzyl, benzoyl, alkoxy, carboxyl, amido, amino, and alkylamino. Examples of such groups are N,N-diethylamino, N-benzoylamino, N-methoxyamino, N-carboethoxyamino, and N-chloroethylamino groups. Also, both the substituents on the amino group can be combined together to form 5 or 6-membered cyclic ring system represented by pyrrolidino, piperidino, piperizino, morphilino, imidazolino, or thiazolidino.

According to the present invention there is provided a process for the preparation of the compounds of the general formula 1,

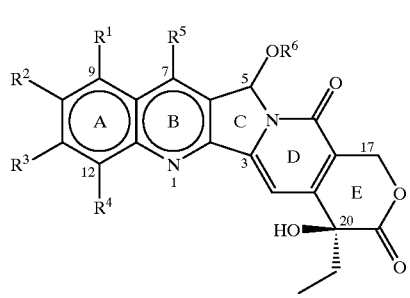

1 wherein $R^1$, $R^2$, $R^3$, $R^4$ are independently the same or different and represent hydrogen, hydroxy, aryloxy, lower alkoxy, lower alkanoyl, nitro, cyano, halo, carboxy, carbonyloxy, amino, substituted amino, lower alkyl, substituted lower alkyl or $R^2$, $R^3$ together represent $—O—(CH_2)_n—O—$ where n=1 or 2; $R^5$ represents hydrogen, lower alkyl, substituted lower alkyl, lower aralkyl, hydroxymethyl, carboxymethyl, aminomethyl, substituted aminomethyl where the amino group may be mono or disubstituted in which both substituents are independent or combined together to form a cyclic ring system of a total of 5–6 atoms containing carbon and optionally one or two heteroatoms selected from oxygen, nitrogen or sulfur; and $R^6$ represents hydrogen; phenyl or benzyl where the phenyl group may be unsubstituted or substituted with mono, di or trisubstituents which may be selected from halogen, hydroxy, lower alkoxy, cyano, carboxyl, nitro, amino or substituted amino, lower alkyl, substituted lower alkyl; cycloalkyl or cycloalkyl lower alkyl where the cyclic ring is in the range of 3 membered to 7 membered ring system containing all carbon atoms; lower alkyl groups substituted with heterocyclic rings where the heterocyclic ring system has a total of 3 to 7 atoms, the ring system contains carbon with at least one heteroatom such as oxygen, nitrogen or sulfur; lower alkanoyl; benzoyl where the phenyl group can be unsubstituted or substituted; lower alkenyl; lower alkyl; substituted lower alkyl, substituted lower alkenyl or substituted lower alkanoyl where the substituents can be halogen, hydroxy, lower alkoxy, aryloxy, thio, thioalkyl, thioaryl, aryl or heteroaryl, carboxy, cyano, nitro, amido or amino in which the amino group can be unsubstituted or mono, or disubstituted in which both substituents are independent or combined together to form 5 or 6 membered cyclic ring system containing carbon, and optionally contains one or two heteroatoms selected from oxygen, nitrogen or sulfur, the total number of atoms in the cyclic ring system being 5 or 6; with the proviso that (i) when $R^1$ is methoxy group, $R^6$ is not hydrogen or lower alkyl group; (ii) when $R^2$ is hydroxy, lower alkoxy, thioalkyl, nitro, amino, alkylamino, acylamino, and halogen, $R^6$ is not hydrogen or lower alkyl group; (iii) when $R^5$ is lower alkyl, lower aralkyl, $CH_2OH$, COOR, COOMe, or $CH_2OR''$ where $R''$ represents lower alkyl or acyl group, $R^6$ is not hydrogen or lower alkyl group (iv) when $R^1$ is methoxy group, $R^2$ is hydroxy, lower alkoxy, thioalkyl, nitro, amino, alkylamino, acylamino, or halogen, $R^5$ is lower alkyl, lower aralkyl, $CH_2OH$, COOH, COOMe or $CH_2OR''$0 where $R''$ represents lower alkyl or acyl group, $R^6$ is not hydrogen or lower alkyl group; (v) when $R^1$ through $R^5$ represent hydrogen, $R^6$ is not hydrogen or lower alkyl group, which comprises, (i) reacting the compounds of the formula 2,

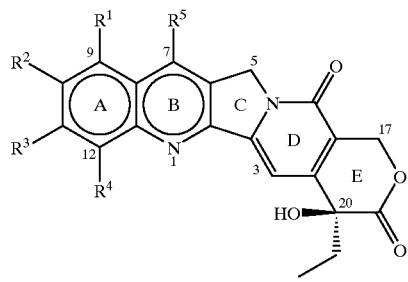

where $R^1$ to $R^5$ have the meaning described above, in the presence of an acid and an oxidizing agent which is a ferric salt, with a compound having the formula $R^6$—OH where $R^6$ represents lower alkyl, lower alkenyl, $(C_3$–$C_7)$cycloalkyl, haloalkyl or hydroxyalkyl, to obtain compounds of the formula 12 and compounds of the formula 13,

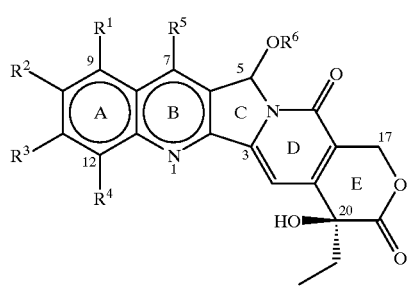

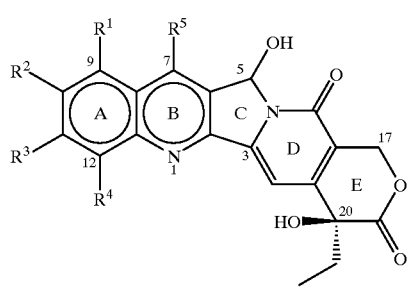

wherein $R^1$, $R^2$, $R^3$, $R^4$, $R^5$ have the meaning given above, (ii) separating the compounds of the formulae 12 and 13 prepared in the step (i), by conventional methods, (iii) hydrolyzing the compounds of the formula 12, by conventional methods, to obtain additional amounts of the compounds of the formula 13, (iv) reacting the compound of the formula 13, in the presence of an acid, with a compound having the formula $R^6$—OH to obtain compounds of the formula 1,

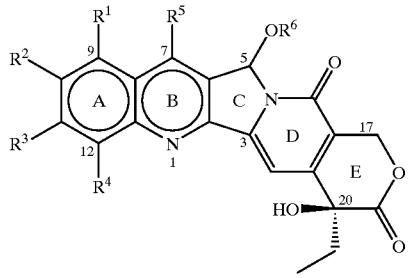

where $R^1$, $R^2$, $R^3$, $R^4$ and $R^5$ have the meaning described above and $R^6$ is as defined above.

According to another feature of the present invention there is provided an alternate process for the preparation of known C-5 substituted compounds of the formula 1,

1

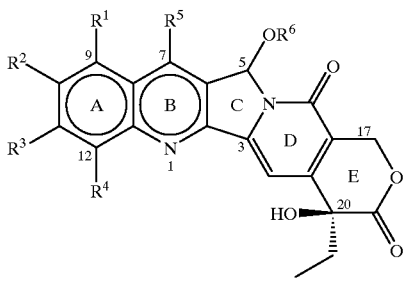

wherein $R^6$ represents hydrogen or lower alkyl, $R^1$ represents hydrogen or methoxy; $R^2$ represents hydrogen, hydroxy, lower alkoxy, acyloxy, thioalkyl, SH, thioacyl, nitro, amino, alkylamino, acylamino and halogen; $R^3$ and $R^4$ are hydrogen and $R^5$ represents hydrogen, lower alkyl, lower aralkyl, $CH_2OH$, COOH, COOMe or $CH_2OR'$ where R' represents lower alkyl or acyl group which comprises, (i) reacting the compounds of the formula 2,

2

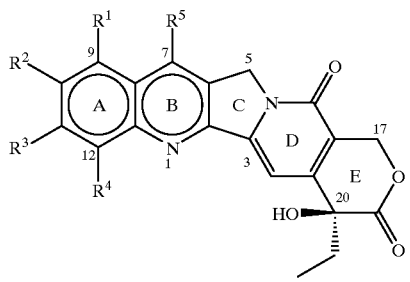

where $R^1$ to $R^5$ have the meaning described above, in the presence of an acid and an oxidizing agent such as ferric salt, with a compound having the formula $R^6$—OH where $R^6$ represents lower alkyl groups, to obtain compounds of the formula 12 and compounds of the formula 13,

12

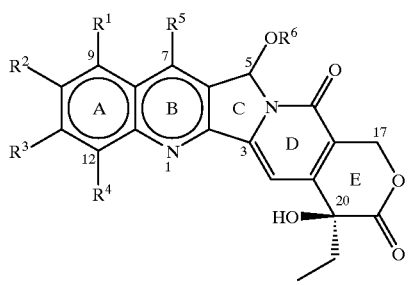

-continued

13

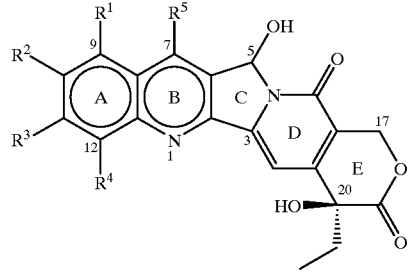

wherein $R^1$, $R^2$, $R^3$, $R^4$ and $R^5$ have the meaning given above, (ii) separating the compounds of the formulae 12 and 13 prepared in the step (i), by conventional methods, (iii) hydrolyzing the compounds of the formula 12, by conventional methods, to obtain additional amounts of the compounds of the formula 13, (iv) reacting the compound of the formula 13, in the presence of an acid, with a compound having the formula $R^6$—OH to obtain compounds of the formula 1, $R^6$ represents lower alkyl groups, $R^1$ represents hydrogen or methoxy, $R^2$ represents hydrogen or hydroxy, lower alkoxy, acyloxy, SH, thioalkyl, thioacyl, nitro, amino, alkylamino, acylamino and halogen; $R^3$ and $R^4$ are hydrogen and $R^5$ represents hydrogen, lower alkyl, lower aralkyl $CH_2OH$, COOH, COOMe or $CH_2OR'$ where R' represents lower alkyl or acyl group.

The methodology developed and described in the present invention has generated a new chiral center at C-5 position in the compounds of formula 2 without disturbing the integrity of 20(S)-α-hydroxy E-ring lactone moiety. The process developed constitutes a novel, facile and versatile semi-synthetic method for the preparation of C-5 substituted known and novel camptothecin derivatives of the formula 1, starting from the compounds of formula 2. The compounds of the formula 1 prepared by the process of the present invention thus represents diastereomers containing the newly created C-5 chiral center. Indeed, the compounds of the general formula 1 are isolated as a mixture of 20(S),5(R) and 20(S),5(S) diastereomers. However, by the application of conventional analytical techniques, the two diastereomers have also been separated into their single optically pure entities.

In general, all of compounds of the formula 1 where $R^1$, $R^2$, $R^3$, $R^4$, $R^5$ and $R^6$ have the meaning described above, may be synthesized starting from the compounds of the formula 2 by the process described above and can be illustrated with the examples described in the Examples Section. The preparation of the compounds of the formula 12, where $R^1$, $R^2$, $R^3$, $R^4$, $R^5$ and $R^6$ have the meaning given above, from the compounds of the formula 2 as mentioned in the step (i), is a novel transformation in which a direct introduction of various types of alkoxy substituents at C-5 position has been achieved.

The A ring or A/B ring substituted 20(S)-camptothecin derivatives of the general formula 2 where $R^1$, $R^2$, $R^3$, $R^4$ and $R^5$ have the meaning described above, used as starting materials in the present invention are widely known and prepared according to the prior art documented in the literature. For example, 7-ethylcamptothecin, 10-hydroxycamptothecin, 9-nitrocamptothecin, 12-nitrocamptothecin, 10-hydroxy-7-ethylcamptothecin (SN-38), 9-amino-camptothecin, 9-methoxycamptothecin, 9-hydroxycamptothecin, 9-methoxy-7-ethylcamptothecin, 9-hydroxy-7-ethylcamptothecin, 10,11-methylenedioxycamptothecin, 10,11-ethylenedioxycamptothecin, 10-hydroxy-9-(N,N-dimethylaminomethyl)camptothecin were prepared according to the known literature methods [T. R. Govindachari et al., *Ind. J. Chem.* 10(B), 453(1972); S. Sawada et al, *Chem. Pharm. Bull,* 39(10) 2574 (1991), ibid., 39(12), 3183 (1991); U.S. Pat. No. 4,604,463; and U.S. Pat. No. 4,545,880; Jaffery L. Wood et. al., *J. Org. Chem.,* 60 5739 (1995)] and used as starting materials for the preparation of novel C-ring substituted 20(S)-camptothecin analogues of the general formula 1 described in the present invention.

For example, compounds of the formula 12 where $R^1$, $R^2$, $R^3$, $R^4$, $R^5$ and $R^6$ are independently the same or different and have the meaning given above, can be prepared, as mentioned in the step (i), by the reaction of the compounds of the formula 2 with the compounds having the formula $R^6$—OH where $R^6$ represents hydrogen, lower alkyl, lower alkenyl, haloalkyl, hydroxyalkyl, ($C_3$–$C_7$) cycloalkyl, in the presence of a strong acid and a ferric salt. The acids used in this reaction can be selected from perchloric acid, hydrochloric acid, nitric acid, sulfuric acid or Lewis acids such as boron-trifluoride, zinc chloride, tinchloride, titanium tetrachloride. The ferric salt used in the above reaction can be chosen from ferric nitrate, ferric ammonium sulfate, ferric chloride. In general, the above reaction may be affected at a temperature in the range of 40–150° C., preferably 60 to 120° C.

In step (ii) of the process of the present invention, to separate the mixture of compounds of formulas 12 and 13 as prepared in the step (i) the mixture is subjected to preferably either crystallization or column chromatography technique using silica gel. The solvent mixtures used in the above mentioned methods may contain a combination of the organic solvents such as chloroform, ethyl acetate, methanol, ethanol, ether, acetone and hexane.

The compounds of the formula 13 can also be obtained in step (iii) of the process of the present invention, by treating the compounds of the formula 12 with acids in combination with water at a temperature in the range of 40–120° C. The acids used for this purpose may be selected from hydrochloric acid, hydrobromic acid, sulfuric acid, p-toluenesulfonic acid, acetic acid and perchloric acid. The solvents used in the reaction may be methanol, ethanol, butanol, isopropanol or 1,4-dioxane.

In step (iv) of the process of the present invention, compounds of the formula 13 were reacted with compounds of the formula $R^6$—OH where $R^6$ has the meaning described above, in the presence of an acid medium at a temperature in the range of 20 to 140° C. to furnish the compounds of the formula 1. The acids used in the reaction may be selected from sulfuric acid, hydrochloric acid, acetic acid, p-toluenesulfonic acid, pyridinium-p-toluenesulfonic acid, camphorsulfonic acid, methanesulfonic acid, perchloric acid or Lewis acids such as titanium tetrachloride, $BF_3$-etherate and zinc chloride. The solvents used in the reaction may be selected from hexane, benzene, toluene, xylene, chloroform, carbon tetrachloride, dichloroethane, dichloromethane and 1,4-dioxane.

Thus, the present invention is of particular significance in developing C-5-substituted 20(S)-camptothecin derivatives as a new class of C-ring modified camptothecin analogues which are useful as anti-tumor and/or anti-viral agents. The present invention is also of particular significance as the process developed and described here is highly versatile and amenable for large scale preparation of these camptothecin derivatives having the general formula 1.

The methodology developed and described in the present invention will provide access to a wide variety of C-5 substituted C-ring analogues having diverse substituents on rings A and B of 20(S)-camptothecin. Some of the preferred compounds are those where $R^1$ is nitro, amino, aminoalkyl, hydroxy, methoxy; $R^2$ is hydroxy, carbonyloxy, halo; $R^2$, $R^3$ combined together to represent methylenedioxy or ethylenedioxy; $R^4$ is hydrogen or nitro; $R^5$ is ethyl, aminomethyl or substituted aminomethyl; $R^6$ is 2'-hydroxyethyl, alkoxyethyl, chloroethyl, fluoroethyl, trifluoro-ethyl, or aminoethyl or aminopropyl where amino group may be dimethylamino, diethylamino, pyrollidino, piperidino, morphilino, piperizino, imidazolino; Representative of the compounds of formula 1 are:

1) 5-methoxy CPT*
2) 5-ethoxy CPT*
4) 5-butoxy CPT*
5) 5-chloroethoxy CPT*
6) 9-methoxy-5-ethoxy CPT
7) 9-hydroxy-5-ethoxy CPT
8) 10-hydroxy-5-ethoxy CPT*
9) 7-ethyl-5-ethoxy CPT*
10) 7-ethyl-5-hydroxy CPT*
11) 9-nitro-5-ethoxy CPT
12) 9-nitro-5-hydroxy CPT
13) 7-Ethyl-5-chloroethoxy CPT
14) 10-hydroxy-7-ethyl-5-ethoxy CPT*
15) 5-(2'-hydroxyethoxy) CPT
16) 7-ethyl-9-hydroxy-5-ethoxy CPT
17) 10-hydroxy-5-(2'-hydroxyethoxy) CPT
18) 7-ethyl-10-hydroxy-5-(2'hydroxyethoxy) CPT
19) 9-nitro-5-fluoroethoxy CPT
20) 9-nitro-5-trifluoroethoxy CPT
21) 10-hydroxy-5-trifluoroethoxy CPT
22) 7-ethyl-10-hydroxy-5-trifluoroethoxy CPT
23) 7-ethyl-5-pyrrolidinoethoxy CPT
24) 7-ethyl-5-dimethylaminopropoxy CPT
25) 7-ethyl-10-hydroxy-5-fluoroethoxy CPT
26) 5-(2'-hydroxyethoxy)-7-ethyl CPT
27) 5-(2'-methoxyethoxy) CPT where CPT refers to 20(S)-camptothecin and * represents known compounds in the literature.

Most of the compounds prepared by the present invention have water solubility ranging from 1 mg to 10 mg per ml at 37° C. Table 1A shows MTD in Swiss Albino mice, Lactone Stability in whole blood (after 3 hours), Solubility, Pharmacokinetics MTD, and In vitro activity after 1 hour exposure, for the compounds of Examples 11, 26 and 27.

The protocols used for conducting the experiments are:

1. MTD in Swiss albino mice:

Each Swiss albino mouse is injected with a single does of the test compound on a day designated as Day 1: Doses that were tested are 400, 200, 100, 50, 25, 12.5, 8.3, 6.25 and 3.13 mg/kg body weight. The animals were observed for mortality and morbidity daily and the body weights of surviving animals were recorded on days 1, 5, 10 and 14. The maximum tolerated dose is defined as the dose at which the test compound did not exhibit any morbidity and body weight reduction more than 30% as compared to day one. (As per the protocol followed by the U.S. National Cancer Institute)

2. Lactone Stability in whole blood:

2 ml of blood from a healthy volunteer was collected in a tube containing 40 μl of heparin (572 IU) to prevent coagulation, 4 mM and 40 μM working solutions of the drug in DMSO were prepared and added to aliquots of whole blood to give final concentration of 100 μM and 1 μM respectively. The drug is incubated in whole blood at 37° C. and 20 µl samples are collected into 180 µl of chilled methanol (−30° C.) at different time intervals (0, 1, 2 & 3 hrs). Vortex and then centrifuge at 11000 rpm for 3 min in a microcentrifuge at room temperature. Dilute 100 µl of the supernatant with water to 300–500 µl depending upon the signal response (UV for 100 µM concentration and fluorescence for 1 µM concentration) of the compound. 200 µl of the diluted sample is injected on to the HPLC column previously equilibrated with the mobile phase. The area under peak corrsponding to lactone forms is measured. Zero time peak area is taken as 100%, and the proportion of lactone peak area at different time points is calculated to determine the equilibrium lactone stability as obtained by consistent lactone proportion over two successive time points. (*Biochemistry*, 1994; 33:10325–10336 and *J. Pharm. Sci.*, 1995; 84:518–519).

3. Pharmacokinetics at MTD:

All studies were carried out in Swiss albino mice in the weight range 35–40 g. The animals were fasted overnight prior to dosage of the drug and were fed 3 hours after dosing. The animals were dosed intra-peritonially as a solution in DMSO:water (50:50; v/v). Blood samples were drawn from orbital sinus at 1, 2, 4, 6 and 8 hours after administration of the dose into heparinized tubes, centrifuged at 13000 RPM for 10 min. Plasma samples were separated and analyzed by HPLC. To 50 µl of the sample, 100 µl of chilled acidified methanol was added and mixed to precipitate proteins. The sample was centrifuged at 13,000 RPM for 10 min. 100 µl of supernatant was made up to 200 µl with methanol:water (50:50; v/v) and 100 µl was injected on HPLC. Peak area of the drug was used for quantification. Calibration, control and recovery samples were prepared by spiking 50 µl of blank plasma with known amounts of the drug and processed in the same manner as the samples. (*J. Natl. Cancer Inst.*, 1996; 88:817–824).

4. Solubility by HPLC method:

Excess of compound was soaked in 0.5 ml of 0.1M sodium acetate buffer at pH 5.0 for 24 hours at room temperature. The solution was filtered through 0.45 micron PVDF syringe filter (Gelman Sciences). The filtrate was injected into HPLC at different volumes (10 & 20 µl). Chromatograms were recorded. Responses recorded were extrapolated from the calibration curve and the solubility of the compound was calculated. (*J. Med. Chem.*, 1995; 38: 400)

5. Solubility by routine method:

Compound was suspended in 5 ml of deionized water and heated to 37° C. for 10 min. Then, the solution was filtered and the filtrate was evaporated to drying using methanol and the solid residue was weighed.

6. In vitro activity after 1 hour exposure:

Grow the cells in 15 ml of Complete Medium (RPM1-1640 with 10% Fetal bovine serum and 0.2% $NaHCO_3$) for 3–5 days to obtain a cell number of $10^6$ cells/flask. The medium is removed and the attached cells are washed with Phosphate Buffered Saline (PBS). 1 ml of 0.1% Trypsin-EDTA is added and incubated for 5 min at 37° C. Tap the flasks gently and add 5 ml of complete medium. Remove cell suspension and centrifuge at 2000 rpm for 5 min. Discard the supernatant and suspend the pellet in 5 ml of complete medium. Count the cell number in a haemocytometer. Dilute the cell suspension to 10,000 cells/100 µl in complete medium. Plate out 100 µl of cell suspension in each of 96 well microtitre plate and incubate for 24 hrs at 37° C. and 5% $CO_2$. Terminate the reference blank (plated out separately) with 25 µl of 50% cold Trichloroacetic acid (TCA). Incubate for 1 hour at 4° C. Wash the plate (five times) with deionized water. Air dry and preserve the plate at 4° C. for determination of $T_0$ value. Prepare suitable dilution of the test compound in complete medium and add 100 µl to each well to maintain the final concentration ranging between $10^{-4}$M and $10^{-8}$M. Incubate for 1 hr at 37° C. and 5% $CO_2$. Centrifuge the microtitre plate at 1000 rpm for 5 min. Remove the supernatant. Wash the cells twice with 100 µl of PBS to remove the traces of test compound. Add 200 µl of complete medium to each well and incubate for 48 hours at 37° C. and 5% $CO_2$. Terminate the cell growth with the addition of 50 µl of 50% cold TCA. Incubate the plate for 1 hr at 4° C. Wash the plates with deionized water (five times) and air dry. Add 100 µl of Sulforhodamine B solution (0.4% in 1% acetic acid) to each well. Keep at room temperature for 15 minutes. Wash (five times) with 1% acetic acid and air dry. Add 100 µl of 10 mM Trizma base (Sigma), shake gently on plate shaker for 15 minutes and read the optical density at 490 nm in Spectrophotometric plate reader. (as per the protocol followed by the U.S. National Cancer Institute.

TABLE 1A

MTD in Swiss Albino mice

| Route | Example 11 | Example 26 | Example 27 |
|---|---|---|---|
| intraperitoneal | 400 mg | 200 mg | 400 mg |
| intravenous | 100 mg | 25–50 mg | 200 mg |

Lactone Stability in Whole Blood (after 3 hours):

| Concentration | Example 11 | | Example 26 | Example 27 | |
|---|---|---|---|---|---|
| | Diastereomer A | Diastereomer B | | Diastereomer A | Diastereomer B |
| 100 µM | 3.73 ± 1.50 | 6.15 ± 2.53 | — | 4.58 ± 1.72 | 11.9 ± 2.91 |
| 1 µM | — | — | 5.3 | — | — |

Solubility:

| Method | Example 11 | Example 26 | Example 27 |
|---|---|---|---|
| HPLC method | 0.17 mg/ml | 0.8 mg/ml | 0.5 mg/ml |
| By routine method | <1 mg/ml | 6 mg/ml | 2–3 mg/ml |

Pharmacokinetics at MTD

| parameter | Example 11 | Example 26 | Example 27 |
|---|---|---|---|
| $AUC_{0-1}$ (µM.h) | 18.47 ± 2.1 | 561.69 ± 41.8 | 23.10 ± 2.7 |
| $C_{max}$ (µM) | 6.95 ± 1.2 | 264.15 ± 21.9 | 7.4 ± 0.8 |
| $T_{max}$ (hrs) | 1.00 ± 0.0 | 1.0 ± 0.0 | 1.33 ± 0.6 |
| $K_{elim}$ | 0.37 ± 0.07 | 0.38 ± 0.06 | 0.29 ± 0.02 |
| Half life (hrs) | 1.92 ± 0.4 | 1.84 ± 0.3 | 2.38 ± 0.2 |

In vitro activity after 1 hour exposure (GI50 values):

| Cell line | Example 11 | Example 26 | Example 27 |
|---|---|---|---|
| SF-268 | $6 \times 10^{-6}$M | $>10^{-4}$M | $>10^{-4}$M |
| OVCAR-8 | $4.5 \times 10^{-6}$M | $>10^{-4}$M | $7.5 \times 10^{-5}$M |
| MCF-7/ADR | $1.5 \times 10^{-6}$M | $>10^{-4}$M | $6 \times 10^{-5}$M |
| DU-145 | $3.5 \times 10^{-7}$M | $5 \times 10^{-5}$M | $3.5 \times 10^{-7}$M |
| ACHN | $5.5 \times 10^{-7}$M | $>10^{-4}$M | $8 \times 10^{-6}$M |
| HOP-62 | $6 \times 10^{-6}$M | $>10^{-4}$M | $2 \times 10^{-6}$M |
| UACC-62 | $4 \times 10^{-5}$M | $7.5 \times 10^{-8}$M | $9 \times 10^{-6}$M |

Further, several compounds prepared in the present invention exhibited good in vitro anti-cancer activity towards various human tumor cell lines, according to the results obtained from the 60 human tumor cell line assay performed at National Cancer Institute (NCI), Bethesda, Md., U.S.A Table 1 presents in vitro cell line activity expressed as IC50 values for various 20(S)-camptothecin C-ring analogues prepared in the present invention. Charts 1 to 3 present the data compiled based on NCI mean graphs for total growth inhibition (TGI) of different types of human cancer cell lines for the compounds prepared in the examples 27, 28 and 43. Similar data compiled for topotecan based on NCI mean graph is also included for comparison purposes. The data presented in Tables 2 and 3 shows that the C-ring analogues of 20(S)-camptothecin prepared in the present invention exhibited anti-tumor activity equal or superior to topotecan towards certain cell lines of different cancer cell panels. Table 4 presents the data obtained for the compound prepared in the example 32 against AIDS related lymphoma(ARL) cell lines. All the compounds used in the NCI's in vitro anti-cancer screening programme are mixtures substantially containing both the diastereomers having 20(S),5(S) and 20(S),5(R) configurations in varied ratios.

The results shown in charts 1 to 3 and tables 1 to 4 were obtained from conducting experiments according to U.S. National Cancer Institute (NCI) protocols as given below:

Each test compound was screened against a battery of 60 human cell lines obtained from eight organs. In a typical procedure, the cell suspensions that were diluted according to the particular cell type and the expected target cell density (5000–40,000 cells per well based on cell growth characteristics) were added into 96-well microtiter plates. Inoculates were allowed a preincubation period of 24 h at 37° C. for stabilization. Dilutions at twice the intended test concentrations were added at time zero in 100 $\mu$l aliquots to microtiter plate wells. Usually test compounds were evaluated at five 10-fold dilutions. The highest well concentration used in the test is $10^{-4}$M. The cells are then incubated in the presence of drug (the test compound) for further 48 h in 5% $CO_2$ atmosphere and 100% humidity. At the end of this time, the adherent cells are fixed to the plate by means of trichloroacetic acid, and after a number of washes, the cell layer is treated with the protein stain Sulforhodamine B. The optical density which is proportional to protein mass, is then read by automated spectrophotometric plate readers at a wavelength of 515 nm. Readings are transferred to a microcomputer and final reports are generated using especially developed software.

The compounds of formula 1 of the present invention, and the pharmaceutically acceptable salts thereof as described above, and the compositions containing them, are useful as anti-cancer and anti-viral agents. Administration of the novel active compounds of the formula 1, in pure form or in an appropriate pharmaceutical composition can be carried out via any of the accepted modes of administration for serving similar utilities. Thus, administration can be, for example, orally, nasally, parenterally or topically, in the form of solid, semi-solid, lyophilized powder, or liquid dosage forms, such as for example, tablets, suppositories, pills, capsules, powders, solutions, suspensions, emulsions, creams, lotions, aerosols, ointments, injections or the like, preferably, in unit dosage forms suitable, for simple administration of precise dosages. The compositions will include a conventional pharmaceutical carrier, diluent or excipient and an active novel compound of formula 1 and, in addition, may include either medicinal agents, pharmaceutical agents, carriers, adjuvants, etc.

The invention is described in detail with specific examples given below, which are provided by way of illustration only and should not be considered to limit the scope of the invention.

TABLE 1

| S. NO. | COMPOUND | IC50 ($\mu$m)[a] |
|---|---|---|
| 1. | 5-Methoxycamptothecin* | 8.5 |
| 2. | 5-Ethoxycamptothecin* | 9.54 |
| 3. | 5-n-Butoxycamptothecin* | 6.16 |
| 4. | 5-(2'-Hydroxyethoxy)camptothecin | 1.51 |
| 5. | 5-(2'-Chloroethoxy)camptothecin | 4.57 |
| 6. | 7-Ethyl-5-ethoxycamptothecin* | 1.41 |
| 7. | 9-Methoxy-7-ethyl-5-ethoxycamptothecin | 2.13 |
| 8. | 7-Ethyl-5-chloroethoxy camptothecin | 2.75 |
| 9. | 7-Ethyl-5-aminoethoxy camptothecin | 18.6 |
| 10. | 7-Ethyl-5-pyrollidinoethoxy camptothecin | 18.6 |
| 11. | 7-Ethyl-5-piperidinoethoxy camptothecin | >30 |
| 12. | 7-Ethyl-5-N,N-dimethylaminoethoxy camptothecin | 13.8 |
| 13. | 7-Ethyl-5-N,N-dimethylaminopropoxy camptothecin | >30 |
| 14. | 9-Methoxy-5-ethoxy camptothecin | 2.45 |
| 15. | 5-Trifluoroethoxy camptothecin | 1.82 |
| 16. | 5-Aminoethoxy camptothecin | 30.0 |
| 17. | 7-Ethyl-5-trifluoroethoxycamptothecin | 7.41 |
| 18. | 7-Ethyl-5-(2'-hydroxyethoxy)camptothecin | 4.78 |
| 19. | 5-Fluoroethoxycamptothecin | 1.58 |
| 20. | 10-Hydroxy-5-trifluoroethoxy camptothecin | 0.38 |
| 21. | 9-Nitro-5-trifluoroethoxy camptothecin | 0.46 |
| 22. | 10-Hydroxy-5-(2'hydroxyethoxy)camptothecin | 8.12 |
| 23. | 9-Nitro-5-(2'-hydroxyethoxy)camptothecin | 7.94 |
| 24. | 7-Ethyl-5-fluoroethoxy camptothecin | 4.36 |
| 25. | 5-Methoxyethoxy camptothecin | 2.23 |
| 26. | 9-Nitro-5-methoxyethoxy camptothecin | 2.04 |
| 27. | 12-Nitro-5-ethoxy-camptothecin | >30 |
| 28. | 12-Nitro-5-hydroxy camptothecin | >30 |
| 29. | 9-Amino-5-methoxy camptothecin | 6.76 |
| 30. | 9-Hydroxy-5-ethoxy camptothecin | 6.68 |

[a]IC50 = the mean value of the minimum drug concentration ($\mu$m) of the agent required to produce 50% cell growth inhibition (GI50) against NCI's 60 human tumor cell line assay.
*represents C-5 substituted camptothecin derivatives known in the literature.

TABLE 2

| CELL PANEL | LEUKEMIA | CNS | | BREAST | COLON |
|---|---|---|---|---|---|
| CELL LINE | MOLT 4 | SF 295 | U 251 | MCF 7 | HT 29 |
| TOPOTECAN | 1.2 | 2.18 | 2.81 | 100 | >100 |
| EXAMPLE 25 | 3.0 | 2.15 | 3.57 | 9.2 | 7.90 |

TABLE 3

| CELL PANEL | NSLC | | | COLON CANCER | | | OVARIAN | | RENAL | | CNS |
|---|---|---|---|---|---|---|---|---|---|---|---|
| CELL LINE | EKVX | H 460 | H 322M | HCC 2998 | HT 29 | HCT 15 | SK-OV3 | OVCAR 8 | UO 31 | SF 268 | U 251 |
| TOPOTECAN | 100 | 1.2 | 16.9 | 15.8 | >100 | 44.6 | 5.12 | 18.19 | 2.51 | 56 | 2.81 |
| EXAMPLE 26 | 63 | 1.0 | 31.6 | 10.47 | 46 | 36.3 | 3.80 | 13.4 | 3.89 | 30.9 | 7.58 |

All the above values refer to Total Growth Inhibition *(TGI) in μm (micromolar) concentrations.

*TGI refer to minimum concentrations of the agent (test compound) required to produce total cell growth inhibition in the NCI's in vitro 60 human tumor cell line assay.

TABLE 4

In vitro activity of Example 32 against AIDS related Lymphoma (ARL) cell lines:

| Cell Name | GI50* | TGI** |
|---|---|---|
| CCRF - CEM | 0.318 | 1.83 |
| RL | 0.463 | 3.94 |
| KD 488 | 0.246 | 2.28 |
| AS 283 | 0.268 | 0.678 |
| PA 682 | 0.456 | 7.23 |
| SU-DHL-7 | 0.609 | 3.51 |

*GI50 refers to the minimum concentration(μm) of the test compound required for 50% cell Growth Inhibition.
**TGI refer to minimum concentration (μm) of the test compound required for the Total Growth Inhibition.

CHART 1

In vitro ANTI-CANCER activity data of Example 27
(The data shown here refers to Total growth Inhibition (TGI) values in μm concentrations)

NSLC:

| CELL LINES | HOP 62 | HOP 92 | H 226 | H 23 | H 460 | H 522 |
|---|---|---|---|---|---|---|
| EXAMPLE 27 | 4.95 | 4.88 | 4.75 | 0.91 | 5.09 | 7.66 |
| TOPOTECAN | 0.04 | 7.90 | 10.96 | 0.87 | 1.20 | 4.16 |

COLON CANCER:

| CELL LINES | COLO 205 | HCC 2998 | HCT 116 | HCT 15 | HT 29 | KM 12 |
|---|---|---|---|---|---|---|
| EXAMPLE 27 | 19.5 | 7.67 | 4.06 | 20.0 | 2.41 | 10.6 |
| TOPOTECAN | 7.94 | 15.8 | 2.51 | 44.6 | 100 | 6.45 |

BREAST CANCER:

| CELL LINES | MCF 7/ADR | MDA-MB-435 | MDA-N | BT 549 | T 47D |
|---|---|---|---|---|---|
| EXAMPLE 27 | 1.25 | 9.62 | 11.0 | 11.4 | 0.81 |
| TOPOTECAN | 1.50 | 2.5 | N.D. | >100 | 1.8 |

CHART 2

In vitro ANTI-CANCER activity data of Example 28
(The data shown here refers to Total growth Inhibition (TGI) values in μm concentrations)

NSLC:

| CELL LINES | HOP 92 | H 226 | H 23 | H 322M | H 460 | H 522 |
|---|---|---|---|---|---|---|
| EXAMPLE 28 | 8.44 | 4.3 | 0.76 | 30.2 | 1.22 | 13.0 |
| TOPOTECAN | 7.90 | 10.96 | 0.87 | 16.9 | 1.20 | 4.16 |

COLON CANCER

| CELL LINES | COLO 205 | HCC 2998 | HCT 116 | HCT 15 | HT 29 | KM 12 |
|---|---|---|---|---|---|---|
| EXAMPLE 28 | 9.48 | 7.65 | 8.01 | >30 | 7.94 | 27.4 |
| TOPOTECAN | 7.94 | 15.80 | 2.51 | 44.6 | 100 | 6.45 |

CHART 2-continued

In vitro ANTI-CANCER activity data of Example 28
(The data shown here refers to Total growth Inhibition (TGI) values in μm concentrations)

BREAST CANCER:

| CELL LINES | MCF7/ADR | MDA-MB-435 | BT 549 | MDA-N | T 47D |
|---|---|---|---|---|---|
| EXAMPLE 28 | 1.21 | 11.4 | 32 | 13.4 | 1.09 |
| TOPOTECAN | 1.5 | 2.5 | >100 | N.D. | 1.8 |

RENAL CANCER:

| CELL LINES | 786-O | A 498 | ACHN | CAKI | RXF 393 | SN12C | UO 31 |
|---|---|---|---|---|---|---|---|
| EXAMPLE 28 | 0.85 | 1.76 | 0.37 | 0.75 | 15.9 | 2.31 | 1.23 |
| TOPOTECAN | 0.12 | 1.69 | 0.28 | 0.51 | 1.41 | 1.58 | 2.51 |

CHART 3

In vitro ANTI-CANCER activity data of Example 43
(The data shown here refers to Total growth Inhibition (TGI) values in μm concentrations)

NSLC:

| CELL LINES | HOP 62 | H 226 | H 23 | H 460 |
|---|---|---|---|---|
| EXAMPLE 43 | 3.92 | 6.89 | 2.52 | 14.2 |
| TOPOTECAN | 0.04 | 10.96 | 0.87 | 1.20 |

COLON CANCER:

| CELL LINES | COLO 205 | HCC 2998 | HCT 166 | HT 29 | KM 12 |
|---|---|---|---|---|---|
| EXAMPLE 43 | 37.3 | 23.2 | 23.6 | 18.9 | 41.9 |
| TOPOTECAN | 7.94 | 15.8 | 2.51 | 100 | 6.45 |

BREAST CANCER:

| CELL LINES | MCF7/ADR/RES | MCF 7 |
|---|---|---|
| EXAMPLE 43 | 9.30 | 17.8 |
| TOPOTECAN | 1.5 | 100 |

EXAMPLES

Example 1

Preparation of 5-methoxycamptothecin (known compound)

Step 1: To a mixture of 20(S)-Camptothecin of the formula 3 (2 g), ferric chloride (2 g), dissolved in 80 ml of methanol, 10 ml of sulfuric acid was added dropwise and continued heating at 70° C. for 24 h. Excess acid and methanol were removed under vacuum and the residue was extracted with ethylacetate. Organic layer was washed with water, brine and dried over anh.sodium sulfate. Concentration of the solvent afforded 1.8 g of yellowish powder containing 5-methoxycamptothecin and 5-hydroxy camptothecin in the ratio of 5:1.

Step 2: Separation of the mixture by silica gel column chromatography using methanolchloroform solvent mixture as eluent afforded 1.5 g of 5-methoxycamptothecin and 300 mg of 5-hydroxycamptothecin. Analytical data for 5-methoxycamptothecin: mp: 156° C.; $[\alpha]_D$ at 28° C.=+ 41.74 (c 0.103, CHCl$_3$); IR: 3426, 1747, 1664, 1616, 1228, 1155, 1046, 762 cm$^{-1}$; $^1$H NMR (CDCl$_3$, 200 MHz): δ

8.42(s, 1H), 8.26(d, J=8 Hz, 1H), 7.96(d, J=8 Hz, 1H), 7.88 (t, J=6.8 Hz, 1H), 7.68(t, J=6.8 Hz, 1H), 7.58(s, 0.5H), 7.54(s, 0.5H), 6.95(s, 0.5H), 6.80(s, 0.5H), 5.74(d, J=16.5 Hz, 0.5H), 5.72 (d, J=16.5 Hz, 0.5H), 5.25(d, J=16.5 Hz, 1H), 3.75(s, 1H), 3.70(s, 1.5H), 3.50(s, 1.5H), 2.01–1.82(m, 2H), 1.06(t, J=7 Hz, 3H); Mass (m/z): 379(M+H), 348, 319.

Example 2

Preparation of 5-Hydroxycamptothecin (known compound)

Step 1: Preparation of 5-methoxy camptothecin: 5-Methoxycamptothecin of the formula 1 where $R^1=R^2=R^3=R^4=R^5=H$, $R^6=Me$ was prepared from 20(S)-camptothecin of the formula 3 as described in the example 1.

Step 2: 1.5 g of 5-methoxycamptothecin of the formula 1 where $R^1=R^2=R^3=R^4=R^5=H$, $R^6=Me$ was dissolved in 50 ml of methanol and treated with 50 ml of 50% HCl. The solution was heated to reflux for 30 h. At the end, excess water and methanol were removed as an azeotropic mixture and the residue was extracted with ethylacetate. Organic layer was washed with brine and dried over anh.sodium sulfate. Concentration of the solvent afforded 1.2 g of 5-hydroxycamptothecin after purification over silica gel column chromatography using a solvent mixture of ethyl acetate and chloform; mp: 220° C.; $[\alpha]_D$ at 26° C.=+28.00 (c 0.1 in CHCl$_3$); IR: 3367, 1749, 1658, 1591, 1159, 1046 cm$^{-1}$; $^1$H NMR (CDCl$_3$+DMSO-d6, 200 MHz): δ 8.50 (s, 1H), 8.20 (d, J=8 Hz, 1H), 7.94(d, J=8 Hz, 1H), 7.85(t, J=6.8 Hz, 1H), 7.64(t, J=6.8 Hz, 1H), 7.58 (s, 0.5H), 7.56(s,0.5H), 7.06(s, 0.5H), 7.01(s, 0.5H), 6.95(br d, 1H, D$_2$O exchangeable), 5.67(d, J=16.5 Hz, 1H), 5.25(d, J=16.5 Hz, 1H), 5.05 (br d, 1H, D$_2$O) exchangeable), 2.05–1.86(m,2H), 1.06(t, J=7 Hz, 3H); Mass (m/z): 364(M+1), 348, 320, 277, 236, 91, 57.

Example 3

Preparation of 5-Ethoxy-7-ethylcamptothecin (known compound)

Step 1: To a mixture of 7-ethylcamptothecin of the formula 2 where $R^1=R^2=R^3=R^4=H$, $R^5=Et$(1.5 g), ferric chloride (1.35 g), dissolved in 150 ml of ethanol, 9 ml of sulfuric acid was added dropwise and continued heating at 85° C. for 30 h. Excess acid and ethanol were removed under vacuum and the residue was extracted with ethylacetate. Organic layer was washed with water, brine and dried over anh.sodium sulfate. Concentration of the solvent afforded 1.6 g of brownish powder containing 5-ethoxy-7-ethylcamptothecin and 5-hydroxy-7-ethylcamptothecin in the ratio of 10:1.

Step 2: Separation of the mixture by column chromatography gave 1 g of 5-ethoxy-7-ethyl-camptothecin and 100 mg of 5-hydroxy-7-ethylcamptothecin; mp: 150° C.; $[\alpha]_D$ at 27° C.=+10.526 (c 0.085, CHCl$_3$); IR: 3419, 1751, 1662, 1613, 1157, 1075, 1050, 764 cm$^{-1}$; $^1$H NMR (CDCl$_3$, 200 MHz): δ 8.20(d, J=8 Hz, 1H), 8.15(d, J=8 Hz, 1H), 7.81(t, 3=6.8 Hz, 1H), 7.66(t, 7.3 Hz, 1H), 7.54(s, 0.5H), 7.51(s, 0.5H), 7.01(s, 0.5H), 6.89(s, 0.5H), 5.72(d, J=16.5 Hz, 0.5H), 5.71(d, J=16.5 Hz,0. 5H), 5.28(d, J=16.5 Hz, 0.5H), 5.26(d, J=16.5 Hz, 0.5H), 4.3–3.6(m, 3H), 3.5–3.1 (m, 2H), 2.05–1.71(m, 2H), 1.45(t, J=7.5 Hz, 3H), 1.06(t, J=7 Hz, 3H).

Example 4

Preparation of 5-Hydroxy-7-ethylcamptothecin (known compound)

Step 1: Preparation of 5-Ethoxy-7-ethylcamptothecin: 5-Ethoxy-7-ethylcamptothecin of the formula 1 where $R^1=R^2=R^3=R^4=H$, $R^5=R^6=Et$, was prepared from 20(S)-camptothecin of the formula 2 as described in the example 3.

Step 2: 50 ml of 25% H$_2$SO$_4$ was added to 1.0 g of 5-ethoxy-7-ethylcamptothecin of the formula 1 where $R^1=R^2=R^3=R^4=H$, $R^5=R^6=Et$, dissolved in 30 ml of ethanol and heated to reflux for 30 h. At the end, excess water and ethanol were removed as an azeotropic mixture and the residue was extracted with ethylacetate. Organic layer was washed with brine and dried over anh.sodium sulfate. Concentration of the solvent afforded 700 mg of 5-hydroxy-7-ethylcamptothecin after purification over silica gel column chromatography; mp: 252° C.; IR: 3349, 1752, 1656, 1605, 1159, 1054, 766 cm$^{-1}$; Partial data of $^1$H NMR (CDCl$_3$+DMSO-d6) δ 7.19(br s, 1H, D$_2$O exchangeable), 7.15(s, 0.5H), 7.05(s, 0.5H), 5.75(br s, 1H, D$_2$O exchangeable), 5.65(d, J=16.5 Hz, 1H), 5.25 (d, J=16.6 Hz, 1H), 3.52–3.19(m, 2H), 1.45(t, J=7.5 Hz, 3H), 1.02(m, 3H).

Example 5

Preparation of 5-Ethoxy-9-methoxycamptothecin of the formula 1 where $R^1$=OMe, $R^2=R^3=R^4=R^5=H$, $R^6=Et$ Step 1: To a mixture of 9-methoxycamptothecin of the formula 2 where $R^1$=OMe, $R^2=R^3=R^4=R^5=H$ (1 g), ferric chloride (500 mg), dissolved in 50 ml of ethanol 10 ml of sulfuric acid was added dropwise and continued heating at 85° C. for 22 h. Excess acid and ethanol were removed under vacuum and the residue was extracted with ethylacetate. Organic layer was washed with water, brine and dried over anh.sodium sulfate. Concentration of the solvent afforded dark brownish powder.

Step 2: Purification of the above residue over column chromatography using silica gel furnished 500 mg of 5-ethoxy-9-methoxycamptothecin of the formula 1 and 300 mg of 5-hydroxy-9-methoxycamptothecin; mp: 235° C.; $[\alpha]_D$ at 30° C.=+34.18 (c 0.093, MeOH); IR: 3436, 748, 1665, 1619, 1461, 1366, 1093, 814 cm$^{-1}$; $^1$H NMR (CDCl$_3$, 200 MHz): δ 8.81(s, 1H), 7.78(m,2H), 7.53(d, J=5.5 Hz, 1H), 6.96(d, J=7 Hz, 1H), 6.88 (s, 1H), 6.77(s, 1H), 5.72(d, J=16 Hz, 0.5H), 5.75(d, J=16 Hz, 0.5H), 5.27(d, J=16 Hz, 1H), 4.24–3.90(m, 2H), 4.06(s, 3H), 3.80(s, 1H, D$_2$O exchangeable), 1.90(m, 2H), 1.31(m,3H), 1.01(m, 3H); Mass (m/z): 422(M+1), 394, 378, 350, 305, 98, 57.

Example 6

Preparation of 5-Hydroxy-9-methoxycamtothecin (known compound)

Step 1: Initially 5-Ethoxy-9-methoxycamptothecin of the formula 1 where $R^1$=OMe, $R^2=R^3=R^4=R^5=H$, $R^6=Et$, was prepared as described in the example 5.

Step 2: 25 ml of 80% HCl was added to 560 mg of 5-ethoxy-9-methoxycamptothecin of the formula 1 where $R^1$=OMe, $R^2=R^3=R^4=R^5=H$, $R^6=Et$, dissolved in 25 ml of ethanol and heated to reflux for 16 h. At the end, excess water and ethanol were removed as an azeotropic mixture and the residue was extracted with ethylacetate. Organic layer was washed with brine and dried over anh.sodium sulfate. Concentration of the solvent afforded 520 mg of 5-hydroxy-9-methoxy-camptothecin after purification over silica gel column chromatography; mp: 162° C.; $[\alpha]_D$ at 30° C.=+39.68 (c 0.012, MeOH); IR: 3398, 1749, 1656, 1616, 1577, 1465, 1383, 1154, cm$^{-1}$; $^1$H NMR (CDCl$_3$+DMSO-d6): δ 8.81(s, 1H), 7.81–7.61(m, 2H), 7.50(d, J=5.5 Hz, 1H), 7.12–6.71 (m, 2H), 5.70(d, J=16 Hz, 1H), 5.30(d, J=16 Hz, 1H), 4.06(s, 3H), 1.98–1.75(m,2H), 1.10–0.98(m,3H); Mass (m/z): 394(M+1), 377, 348, 266, 149, 88, 57.

Example 7

Preparation of 5-Ethoxy-9-methoxy-7-ethylcamptothecin of the formula 1 where $R^1$=OMe,$R^2$=$R^3$=$R^4$=H,$R^5$=$R^6$=Et Step 1: To a mixture of 9-methoxy-7-ethylcamptothecin of the formula 2 where $R^1$=OMe,$R^2$=$R^3$=$R^4$=H, $R^5$=Et (100 mg), ferric chloride (100 mg), dissolved in 32 ml of ethanol 2 ml of sulfuric acid was added dropwise and continued heating at 85° C. for 4 h. Excess acid and ethanol were removed under vacuum and the residue was extracted with ethylacetate. Organic layer was washed with water, brine and dried over anh.sodium sulfate. Concentration of the solvent afforded 120 mg of residue containing 5-ethoxy-9-methoxy-7-ethylcamptothecin and 5-hydroxy-9-methoxy-7-ethylcamptothecin in the ratio of 1:4.

Step 2: Separation of the mixture by column chromatography using the solvent mixture of ethyl acetate-chloroform gave 15 mg of 5-ethoxy-9-methoxy-7-ethylcamptothecin of the formula 1 and 55 mg of 5-hydroxy-9-methoxy-7-ethylcamptothecin; mp: 240° C.; IR: 3443, 1747, 1663, 1609, 1458, 1254, 1160, 1074 cm$^{-1}$; $^1$H NMR (CDCl$_3$, 200 MHz): δ 7.80–7.68(m, 2H), 7.50(s, 0.5H), 7.47(s, 0.5H), 7.01(s, 0.5H), 6.98(d, J=8 Hz, 1H), 6.89(s, 0.5H), 5.76(d, J=16 Hz, 1H), 5.28(d, J=16 Hz, 0.5H), 5.26(d, J=16 Hz, 0.5H), 4.25–3.81(m, 2H), 4.02(s, 3H), 3.72–3.28(m, 2H), 3.15(br s, 1H, D$_2$O exchangeable), 2.02–1.82(m, 2H), 1.37–1.33(m, 3H), 1.05–0.95(m, 3H); Mass (m/z): 451(M+1), 406, 377, 362, 347, 331, 261, 181, 149, 97.

Example 8

Preparation of 5-Hydroxy-9-methoxy-7-ethylcamptothecin of the formula 13 where $R^1$=OMe, $R^2$=$R^3$=$R^4$=H,$R^5$=$R^6$=Et Step 1: Initially 5-Ethoxy-9-methoxy-7-ethylcamptothecin of the formula 1 where $R^1$=OMe, $R^2$=$R^3$=$R^4$=H,$R^5$=$R^6$=Et, was prepared as described in the example 7.

Step 2: 5 ml of 50% HCl was added to 100 mg of 5-ethoxy-9-methoxy-7-ethylcamptothecin of the formula 1 where $R^1$=OMe, $R^2$=$R^3$=$R^4$=H,$R^5$=$R^6$=Et, dissolved in 5 ml of ethanol and heated to reflux for 26 h. At the end, excess water and ethanol were removed as an azeotropic mixture and the residue was extracted with ethylacetate. Organic layer was washed with brine and dried over anh. sodium sulfate. Concentration of the solvent afforded 80 mg of 5-hydroxy-9-methoxy-7-ethylcamptothecin of the formula 13 after purification over silica gel column chromatography; mp: 242° C.; IR: 3440, 1742, 1660, 1610, 1456, 1250, 1160 cm$^{-1}$.

Example 9

Preparation of 5-Ethoxycamptothecin (known compound)

Step 1: To a mixture of 20(S)-Camptothecin of the formula 3 (1 g), ferric chloride (1 g), dissolved in 50 ml of ethanol 12 ml of BF$_3$-etherate was added dropwise and continued heating at 85° C. for 40 h. Excess acid and ethanol were removed under vacuum and the residue was extracted with ethylacetate. Organic layer was washed with water, brine and dried over anh.sodium sulfate. Concentration of the solvent afforded 1 g of yellowish powder containing 17-ethoxycamptothecin and 5-hydroxycamptothecin in the ratio of 6:1.

Step 2: Separation of this mixture by silica gel column chromatography using ethyl acetate hexane solvent mixture as eluent afforded 700 mg of 5-ethoxycamptothecin and 120 mg of previously prepared 5-hydroxycamptothecin; mp: 140° C.; [α]$_D$, at 28° C.=+29.703 (c 0.101, CHCl$_3$); IR: 3423, 1746, 1663, 1616, 1155, 1070, 1040 cm$^{-1}$; Partial $^1$H NMR data in CDCl$_3$: δ 6.9(s, 0.5H), 6.78(s, 0.5H), 4.25–3.85(m, 2H), 3.70(s, 1H), 2.00–1.80(m, 2H), 1.40–1.22(m, 3H), 1.12–0.98(m, 3H); Mass (m/z): 393 (M+1), 378, 362, 348, 319, 247, 219, 57.

Example 10

Preparation of 5-butoxycamptothecin (known compound)

Step 1: To a mixture of 20(S)-Camptothecin of the formula 3 (500 mg), ferric chloride (500 mg), dissolved in 15 ml of n-butanol, sulfuric acid was added dropwise and continued heating at 100° C. for 20 h. Excess acid and n-butanol were removed under vacuum and the residue was extracted with ethylacetate. Organic layer was washed with water, brine and dried over anh.sodium sulfate. Concentration of the solvent afforded powdery material.

Step 2: Purification of the above material by silica gel column chromatography using ethylacetate-hexane solvent mixture as eluent afforded 300 mg of 5-butoxycamptothecin and 50 mg of previously prepared 5-hydroxycamptothecin; mp: 82° C.; [α]$_D$ at 28° C.=+28.00 (c 0.1, CHCl$_3$); Partial $^1$H NMR data in CDCl$_3$: δ 6.92(s, 0.5H), 6.79(s, 0.5H), 4.12–3.75(m, 2H), 3.80(br s, 1H, D$_2$O exchangeable), 2.00–1.82(m, 2H), 1.75–1.52 (m, 2H), 1.50–1.29(m, 2H), 1.15–0.82(m, 6H); Mass (m/z): 422(M+1), 363, 348, 319, 84, 51.

Example 11

Preparation of 5-Ethoxy-9-hydroxycamptothecin of the formula 1 where $R^1$=OH, $R^2$=$R^3$=$R^4$=$R^5$=H,$R^6$=Et Step 1: To a mixture of 9-hydroxycamptothecin of the formula 2 where $R^1$=OH,$R^2$=$R^3$=$R^4$=$R^5$=H, (200 mg), ferric chloride (250 mg), dissolved in 40 ml of ethanol 1.5 ml of sulfuric acid was added dropwise and continued heating at 85° C. for 26 h. Excess acid and ethanol were removed under vacuum and the residue was extracted with 5% methanol-chloroform. Organic layer was washed with water, brine and dried over anh.sodium sulfate. Concentration of the solvent afforded 170 mg of residue containing 5-ethoxy-9-hydroxycamptothecin and 5,9-dihydroxycamptothecin in the ratio of 3:1.

Step 2: Separation of the mixture by column chromatography using the solvent mixture of ethyl acetate-chloroform gave 75 mg of 5-ethoxy-9-hydroxycamptothecin of the formula 1 along with 25 mg of 9,5-dihydroxycamptothecin; mp: 230° C.; IR: 3400, 2920, 1745, 1663, 1597, 1360, 1280, 1228, 1157, 1083, 902, 816 cm$^{-1}$; $^1$H NMR (CDCl$_3$): δ 8.83(s,1H), 7.78 (d, J=6.8 Hz, 1H), 7.67–7.56 (m, 2H), 7.01(s, 0.5H), 6.98(s, 0.5H), 6.91(s, 0.5H), 6.81(s, 0.5H), 5.70(d, J=16 Hz, 1H), 5.33(d, J=16 Hz, 1H), 4.15–3.91(m, 2H), 1.90(m, 2H), 1.05(t, J=7 Hz, 3H); Mass (m/z): 409(M+1), 364, 335, 320, 291, 267, 263, 221, 206, 171, 159, 129, 111, 98, 85.

Example 12

Preparation of 9,5-Dihydroxycamptothecin of the formula 13 where $R^1$=OH,$R^2$=$R^3$=$R^4$=$R^5$=H Step 1: Initially 5-Ethoxy-9-hydroxycamptothecin of the formula 1 where $R^1$=OR, $R^2$=$R^3$=$R^4$=$R^5$=H $R^6$=Et, was prepared as described in the example 11.

Step 2: 25 ml of 80% HCl was added to 560 mg of 5-ethoxy-9-hydroxy camptothecin of the formula 1 where $R^1$=OH, $R^2$=$R^3$=$R^4$=$R^5$=H, $R^6$=Et, dissolved in 25 ml of ethanol and heated to reflux for 16 h. At the end, excess water and ethanol were removed as an azeotropic mixture and the residue was extracted with ethylacetate. Organic layer was washed with brine and dried over anh.sodium sulfate. Concentration of the solvent afforded 320 mg of 9,5-dihydroxycamptothecin of the formula 13 after purification over silica gel column chromatography; mp: 102° C.; IR: 3400, 1744, 1659, 1594, 1462, 1361, 1280, 1229, 1049, 820 cm$^{-1}$: $^1$H NMR (DMSO-d6): δ 10.82 (s, 1H, D$_2$O exchangeable), 7.63–7.69(m, 2H), 7.22(s, 0.5H), 7.19(s, 0.5H), 7.11(d, J=7 Hz, 1H), 6.98(s, 0.5H), 6.95(s, 0.5H), 6.50(s, 1H, D$_2$O exchangeable), 5.42(s, 2H), 1.89(m, 2H), 0.90(t, J=7 Hz, 3H); Mass(m/z): 380(M+1), 320, 305, 293, 264, 235, 206, 191, 160, 128, 96, 85.

Example 13

Preparation of 5-Ethoxy-9-hydroxy-7-ethylcamptothecin of the formula 1 where $R^1$=OH, $R^2$=$R^3$=$R^4$=H, $R^5$=$R^6$=Et Step 1: To a mixture of 9-hydroxy-7-ethylcamptothecin of the formula 2 where $R^1$=OH,$R^2$=$R^3$=$R^4$=H $R^5$=Et, (150 mg), ferric chloride (150 mg), dissolved in 30 ml of ethanol, 2 ml of sulfuric acid was added dropwise and continued heating at 85° C. for 40 h. Excess acid and ethanol were removed under vaccum and the residue was extracted with ethylacetate. Organic layer was washed with water, brine and dried over anh.sodium sulfate. Concentration of the solvent afforded 120 mg of residue containing 5-ethoxy-9-hydroxy-7-ethylcamptothecin and 9,5-dihydroxy-7-ethylcamptothecin in the ratio of 5:1.

Step 2: Separation of the mixture by column chromatography using the solvent mixture of acetone-chloroform gave 85 mg of 5-ethoxy-9-hydroxy-7-ethylcamptothecin of the formula 1 and 15 mg of 5,9-dihydroxy-7-ethylcamptothecin; mp: 240° C.; IR; 3500, 2976, 1749, 1662, 1588, 1555, 1461, 1390, 1147, 1079, 921 cm$^{-1}$; $^1$H NMR (DMSO-d6): δ 10.77(s, 1H D$_2$O exchangeable), 7.62–7.67(m,2H), 7.57(d, J=8 Hz, 1H), 7.08–7.18(m,2H), 6.50(s, 1H, D$_2$O exchangeable), 5.39(s, 2H), 4.08(m, 2H), 3.42(m, 2H), 1.87 (m, 2H), 1.35(t, J=7 Hz, 3H); 0.87(t, J=7 Hz, 3H); Mass (m/z) : 437(M+1), 392, 363, 348, 333, 291, 261, 246, 219, 191, 149, 119, 89.

Example 14

Preparation of 9,5-Dihydroxy-7-ethylcamptothecin of the formula 13 where $R^1$=OH, $R^2$=$R^3$=$R^4$=H, $R^5$=Et Step 1: Initially 5-Ethoxy-9-hydroxy-7-ethylcamptothecin of the formula 1 where $R^1$=OH, $R^2$=$R^3$=$R^4$=H, $R^5$=$R^6$=Et, was prepared as described in the example 13.

Step 2: 35 ml of 80% HCl was added to 560 mg of 5-ethoxy-9-hydroxy-7-ethylcamptothecin of the formula 1 where $R^1$=OH $R^2$=$R^3$=$R^4$=H, $R^5$=$R^6$=Et, dissolved in 25 ml of ethanol and heated to reflux for 16 h. At the end, excess water and ethanol were removed as an azeotropic mixture and the residue was extracted with ethylacetate. Organic layer was washed with brine and dried over anh. sodium sulfate. Concentration of the solvent afforded 380 mg of 5,9-dihydroxy-7-ethylcamptothecin of the formula 13 after purification over silica gel column chromatography; mp: 165° C.: IR 3351, 2929, 1744, 1657, 1606, 1460, 1218, 1162, 1035, 872 cm$^{-1}$: $^1$H NMR (DMSO-d6): δ 10.62 (s, 1H, D$_2$O exchangeble), 7.60–7.57(m, 2H) 7.16–7.00(m, 3H), 5.40(s, 2H, 3.42(q, J=7.6 Hz, 2H), 2.08(m,2H), 1.33(t, J=7 Hz, 3H), 0.89(t, J=7 Hz, 3H); Mass(m/z): 408(M+1), 380, 336, 319, 291, 267, 235, 219, 185, 127, 99, 83.

Example 15

Preparation of 9-nitro-5-ethoxy camtothecin of the formula 1 where $R^1$=NO$_2$, $R^2$=$R^3$=$R^4$=$R^5$=H, $R^6$=Et Step 1: To a mixture of 9-nitrocamptothecin of the formula 2 where $R^1$=NO$_2$ $R^2$=$R^3$=$R^4$=$R^5$=H, (1 g), ferric chloride (1 g), dissolved in 100 ml of ethanol, 10 ml of sulfuric acid was added dropwise and continued heating at 85° C. for 24 h. Excess acid and ethanol were removed under vaccum and the residue was extracted with ethylacetate. Organic layer was washed with water, brine and dried over anh.sodium sulfate. Concentration of the solvent afforded 900 mg of yellowish powder.

Step 2: Purification of the above solid material over silica gel column chromatography using acetone-chloroform solvent mixture as eluent furnished 700 mg of 9-nitro-5-ethoxycamptothecin of the formula 1 and 80 mg of 9-nitro-5-hydroxycamptothecin of the formula 13 where $R^1$=NO$_2$, $R^2$=$R^3$=$R^4$=$R^5$=H; mp: 202° C.; IR (KBr): 3474, 1743, 1668, 1622, 1526, 1344, 1154, 1073, 831cm$^{-1}$; $^1$H NMR (CDCl$_3$, 200 MHz): δ 9.23 (s, 1H), 8.52(d, J=9 Hz, 1H), 8.47(d, J=9 Hz, 1H), 7.92(t, J=8.2 Hz, 1H), 7.55(s, 1H), 6.91(s, 1H), 5.71(d, J=16 Hz, 1H), 5.28(d, J=16 Hz, 1H), 4.39–3.98(m, 2H), 3.75(br s, 1H, D$_2$O exchangeable), 1.99–1.79(m, 2H), 1.32(t, J=7 Hz, 3H), 1.04(t, J=7 Hz, 3H); Mass(m/z): 438(M+1), 407, 393, 364, 349, 319, 262, 118.

Example 16

Preparation of 12-Nitro-5-ethoxycamptothecin of the formula 1 where $R^1$=$R^2$=$R^3$=$R^5$=H, $R^4$=NO$_2$, $R^6$=Et Step 1: To a mixture of 12-nitrocamptothecin of the formula 2 where $R^4$=NO$_2$ $R^1$=$R^2$=$R^3$=$R^5$=H, (2 g), ferric chloride (2 g), dissolved in 150 ml of ethanol, 15 ml of sulfuric acid was added dropwise and continued heating at 85° C. for 24 h. Excess acid and ethanol were removed under vaccum and the residue was extracted with ethylacetate. Organic layer was washed with water, brine and dried over anh.sodium sulfate. Concentration of the solvent gave a gummy solid material.

Step 2: Purification of the above residue over silica gel column chromatography using acetone-chloroform solvent mixture as eluent afforded 1.4 g of yellowish powder containing 12-nitro-5-ethoxycamptothecin of the formula 1 and 100 mg of 12-nitro-5-hydroxycamptothecin of the formula 13 where $R^4$=NO$_2$, $R^1$=$R^2$=$R^3$=$R^5$=H; mp: 250° C.; IR (KBr): 3450, 1750, 1666, 1618, 1525, 1357, 1154, 1042, 766 cm$^{-1}$; $^1$H NMR (CDCl$_3$, 200 MHz); δ 8.49(s, 1H), 8.17(d, J=9 Hz, 1H), 8.14(d, J=9 Hz, 1H), 7.75(t, J=8.2 Hz, 1H), 7.54(s, 1H), 6.95(s, 0.5H), 6.82(s, 0.5H), 5.71(d, J=16 Hz, 1H), 5.26(d, J=16 Hz, 1H), 4.31–3.91(m, 2H), 3.75(m, br s, 1H, $D_2O$ exchangeable), 2.05–1.81(m, 2H), 1.35(1, J=7 Hz, 3H), 1.05(1, J=7 Hz, 3H); Mass (m/z): 438(M+1), 420, 393, 376, 364, 349, 319, 84.

Example 17

Preparation of 10-hydroxy-5-ethoxy camptothecin (known compound)

Step 1: To a mixture of 10-hydroxycamptothecin of the formula 2 where $R^2$=OH, $R^1$=$R^3$=$R^4$=$R^5$=H, (200 mg), ferric chloride (200 mg), dissolved in 10 ml of ethanol, 1.5 ml of sulfuric acid was added dropwise and continued heating at 85° C. for 24 h. Excess acid and ethanol were removed under vaccum and the residue was extracted with 5% methanolethylacetate. Organic layer was washed with water, brine and dried over anh.sodium sulfate. Concentration of the solvent afforded yellow solid material.

Step 2: Purification of the above solid over silica gel column chromatography using acetone-chloroform solvent mixture as eluent provided 100 mg of 10-hydroxy-5-ethoxycamptothecin of the formula 1 and 20 mg of 10,5-dihydroxycamptothecin of the formula 13 where $R^2$=OH, $R^1$=$R^3$=$R^4$=$R^5$=H; mp; 165° C.; IR (KBr) ; 3384, 1747, 1662, 1608, 1229, 1044, 831 cm$^{-1}$; $^1$H NMR(CDCl$_3$+ DMSO, 200 MHz): δ 9.8(1H, br s, $D_2O$ exchangeable), 8.25(s, 1H), 8.05(d, J=6 Hz, 1H), 7.56–7.39(m, 2H), 7.25(s, 1H), 6.85(s, 0.5H), 6.70(s, 0.5H), 5.58(d, J=16 Hz, 1H), 5.35 (d, J=16 Hz, 0.5H), 5.21(d, J=16 Hz, 0.5H), 4.35–3.75(m, 4H), 3.50(br s, 1H, $D_2O$ exchangeable), 2.10–3.78 (m, 2H), 1.22 (t, J=7 Hz, 3H), 1.05(t, J=7 Hz, 3H); Mass (m/z): 409(M+1), 392, 364, 349, 335, 320, 291, 235, 117, 84.

Example 18

Preparation of 10-Hydroxy-7-ethyl-5-ethoxy camptothecin (known compound)

Step 1: To a mixture of 10-hydroxy-7-ethylcamptothecin of the formula 2 where $R^2$=OH, $R^1$=$R^3$=$R^4$=H, $R^5$=Et, (200 mg), ferric chloride (200 mg), dissolved in 10 ml of ethanol, 1.7 ml of sulfuric acid was added dropwise and continued beating at 80° C. for 20 h. Excess acid and ethanol were removed under vacuum and the residue was extracted with ethylacetate. Organic layer was washed with water, brine and dried over anh.sodium sulfate. Evaporation of the solvent gave a solid material.

Step 2: Purification of the above solid residue over silica gel column chromatography using acetone-chloroform solvent mixture as eluent afforded 85 mg of 10-hydroxy-7-ethyl-5-ethoxy-camptothecin as yellowish powder and 20 mg of 10,5-dihydroxy-7-ethylcamptothecin of the formula 13 where $R^2$=OH, $R^1$=$R^3$=$R^4$=H, $R^5$=Et; mp: 190° C.; IR (KBr): 3277, 1746, 1660, 1599, 1231, 1078, 800 cm$^{-1}$; $^1$H NMR (CDCl$_3$+DMSO): δ 9.6(br s, 1H, $D_2O$ exchangeable), 8.01(d, J=8.7 Hz, 1H), 7.51–7.35(m, 3H), 6.92(s, 0.5H), 6.80(s, 0.5H), 5.66(d, J=16 Hz, 1H), 5.22(d, J=16 Hz, 1H), 3.85–3.65(m, 2H), 3.35–2.95(m, 2H), 1.95–1.75(m, 2H), 1.37(t, J=7.4 Hz, 3H), 1.17(t, J=7.2 Hz, 3H), 0.99(t, J=7.4 Hz, 3H); Mass (m/z): 437(M=1), 392, 363, 348, 333, 291, 147, 84.

Example 19

Preparation of 9-amino-5-ethoxycamptothecin of the formula 1 where $R^1$=NH$_2$, $R^2$=$R^3$=$R^4$=$R^5$=H, $R^6$=Et Step 1: To a mixture of 9-aminocamptothecin of the formula 2 where $R^1$=NH$_2$ $R^2$=$R^3$=$R^4$=$R^5$=H, (120 mg), ferric chloride (112 mg), dissolved in 10 ml of ethanol, 1.5 ml of ethereal borontrifluoride(BF$_3$-Et$_2$O) was added dropwise and continued heating at 80° C. for 16 h. Ethanol was removed under vaccum and the residue was extracted with ethylacetate. Organic layer was washed with water, brine and dried over anh.sodium sulfate which upon evaporation of the solvent gave a thick gummy solid.

Step 2: Purification of the above residue over silica gel column chromatography using acetone-chloroform solvent mixture as eluent afforded 65 mg of 9-amino-5-ethoxycamptothecin of the formula 1; mp: 170° C.; IR 3221, 1744, 1661, 1231, 1157, 1074, 815 cm$^{-1}$: $^1$H NMR (CDCl$_3$+ DMSO-d6): δ 8.69(s, 1H), 7.64(s, 1H), 7.63–7.51(m,2H), 7.06(d, J=5.41 Hz, 1H), 6.90(s, 0.5H), 6.80(s, 0.5H), 5.65(d, J=16 Hz, 1H), 5.26(d, J=16 Hz, 1H), 4.19–3.98(m, 1H), 3.97–3.78(m, 1H), 2.98(br s, 3H, $D_2O$ exchangeable), 1.95–1.80(m, 2H), 1.39–1.19(m, 3H), 1.11–0.95(m, 3H) ; Mass(m/z): 407 (M+2), 389, 363, 334, 319, 290, 262, 233, 101.

Example 20

Preparation of 9-amino-5-methoxycamptothecin of the formula 1 where $R^1$=NH$_2$, $R^2$=$R^3$=$R^4$=$R^5$=H, $R^6$=Me Step 1: To a mixture of 9-aminocamptothecin of the formula 2 where $R^1$=$R^2$=$R^3$=$R^4$=$R^5$=H, (180 mg), ferric chloride (162 mg), dissolved in 15 ml of methanol, 2 ml of ethereal borontrifluoride (BF$_3$-Et$_2$O) was added dropwise and continued heating at 80° C. for 16 h. Methanol was removed under vacuum and the residue was extracted with ethylacetate. Organic layer was washed with water, brine and dried over anh.sodium sulfate which upon evaporation of the solvent gave a thick gummy solid.

Step 2: Purification of the above residue over silica gel column chromatography using acetone-chloroform solvent mixture as eluent afforded 125 mg of 9-amino-5-methoxycamptothecin of the formula 1; mp: 200° C.; IR: 3364, 2925, 1744, 1660, 1610, 1156, 1081, 811 cm$^{-1}$; $^1$H NMR (CDCl$_3$+DMSO-d6): δ 8.82 (s, 1H), 7.60(s, 1H), 7.63–7.46(m, 2H), 6.97(d, J=7 Hz, 1H), 6.89(s, 0.5H, 6.80(s, 0.5H), 5.6(d, J=16 Hz, 1H), 5.25(d, J=16 Hz, 1H), 3.57(s, 1.5H), 3.46(s, 1.5H), 3.41(br s, 1H, $D_2O$ exchangeable), 3.15(br s, 2H, $D_2O$ exchangeable), 2.05–1.89(m,2H), 1.01(t, J=7 Hz, 3H); Mass(m/z): 393, (M+1), 376, 363, 349, 334, 319, 290, 262, 233, 205, 116.

Example 21

Preparation of 9-Nitro-5-hydroxy camptothecin of the formula 13 where $R^1$=NO$_2$, $R^2$=$R^3$=$R^4$=$R^5$=H Step 1: Initially 9-nitro-5-ethoxycamptothecin of the formula 1 where $R^1$=NO$_2$, $R^2$=$R^3$=$R^4$=$R^5$=H, $R^6$=Et was prepared as described in the example 15.

Step 2: 80 ml of 50% HCl was added to 1.0 g of 9-nitro-5-ethoxycampothecin of the formula 1 where $R^1$=NO$_2$, $R^2$=$R^3$=$R^4$=$R^5$=H, $R^6$=Et, dissolved in 20 ml of ethanol and heated to reflux for 30 h. At the end, excess water and ethanol were removed as an azeotropic mixture and the residue was extracted with ethylacetate. Organic layer was washed with brine and dried over anh.sodium sulfate. Concentration of the solvent afforded 700 mg of 9-nitro-5-hydroxycamptothecin of the formula 13 after purification over silica gel column chromatography.; mp: 278° C.; IR (KBr): 3402, 1744, 1657, 1602, 1533, 1155, 1051, 833 cm$^{-1}$; $^1$H NMR (CDCl$_3$+DMSO, 200 MHz): δ 9.28(s, 1H), 8.50(d, J=8.6 Hz, 1H), 8.45(d, J=8.6 Hz, 1H), 7.96(t, J=8.2 Hz, 1H), 7.59(s, 0.5H), 7.58(s, 0.5H), 7.12(s, 0.5H), 7.08(s, 0.5H), 5.67(d, J=16 Hz, 1H), 5.27(d, J=16 Hz, 1H), 1.92(q, J=7.2 Hz, 2H), 1.07(t, J=7 Hz, 3H).

Example 22

Preparation of 10,5-Dihydroxy camptothecin
(known compound)

Step 1: Initially 10-Hydroxy-5-ethoxycamptothecin of the formula 1 where R$^2$=OH, R$^1$=R$^3$=R$^4$=R$^5$=H, R$^6$=Et was prepared as described in the example 17.

Step 2: 10 ml of 50% HCl was added to 250 mg of 10-hydroxy-5-ethoxycamptothecin of the formula 1 where R$^2$=OH, R$^1$=R$^3$=R$^4$=R$^5$=H, R$^6$-Et, dissolved in 10 ml of ethanol and heated to reflux for 20 h. At the end, excess water and ethanol were removed as an azeotropic mixture and the residue was extracted with ethylacetate. Organic layer was washed with brine and dried over anh.sodium sulfate. Concentration of the solvent afforded 210 mg of 10,5-dihydroxycamptothecin of the formula 13 after purification over silica gel column chromatography.; mp: 240° C.; IR (KBr): 3226, 1743, 1659, 1596, 1382, 1231, 1048, 832 cm$^{-1}$; $^1$H NMR (CDCl$_3$+DMSO): δ 10.0 (br s, 1H, D$_2$O exchangeable), 8.31(s, 0.5H), 8.29(s, 0.5H), 8.05(d, J=6 Hz, 0.5H), 7.95(d, J=6 Hz, 0.5H), 7.95 (d, J=6 Hz, 0.5H), 7.50–7.31(m, 2H), 7.21(s, 1H), 6.95(s, 0.5H), 6.85(s, 0.5H), 5.55(d, J=16 Hz, 1H), 5.25(d, J=16 Hz, 1H), 3.99(br s, 1H, D$_2$O exchangeable), 2.05–1.81(m, 2H), 1.0(t, J=7 Hz, 3H); Mass (m/z): 381(M+1), 352, 336, 320, 264, 149, 83.

Example 23

Preparation of 12-Nitro-5-hydroxy camptothecin of the formula 13 where R$^1$=R$^2$=R$^3$=R$^5$=H, R$^4$=NO$_2$ Step 1: Initially 12-nitro-5-ethoxycamptothecin of the formula 1 where R$^4$=NO$_2$, R$^1$=R$^2$=R$^3$=R$^5$=H, R$^6$=Et was prepared as described in the example 16.

Step 2: 125 ml of 50% HCl was added to 2 g of 12-nitro-5-ethoxycamptothecin of the formula 1 where R$^4$=NO$_2$, R$^1$=R$^2$=R$^3$=R$^5$=H, R$^6$=Et, dissolved in 30 ml of ethanol and heated to reflux for 24 h. At the end, excess water and ethanol were removed as an azeotropic mixture and the residue was extracted with ethylacetate. Organic layer was washed with brine and dried over anh.sodium sulfate. Concentration of the solvent afforded 1.5 g of 12-nitro-5-hydroxycamptothecin of the formula 13 after purification over silica gel column chromatography; mp: 247° C.: IR (KBr): 3371, 1746, 1664, 1602, 1532, 1380, 1048, 829 cm$^{-1}$; $^1$H NMR (CDCl$_3$, 200 MHz) : δ 8.58(s, 1H), 8.17(d, J=9 Hz, 1H), 8.12(d, J=9 Hz, 1H), 7.74(t, J=8.2 Hz, 1H), 7.58(s, 1H), 7.12(s, 0.5H), 7.08(s, 0.5H), 5.71(d, J=16 Hz, 1H), 5.26(d, J=16 Hz, 1H), 3.90(br s, 1H, D$_2$O exchangeable), 1.99–1.85(m, 2H), 1.05(t, J=7 Hz, 3H); Mass (m/z): 409(M+1), 393, 380, 363, 348, 333, 318, 149, 85.

Example 24

Preparation of 5-(2'-Chloroethoxy)camptothecin of the formula 1 where R$^1$=R$^2$=R$^3$=R$^4$=R$^5$=H, R$^6$=CH$_2$CH$_2$Cl Step 1: To a mixture of 20(S)-Camptothecin of the formula 3 (1 g), ferric chloride (1 g), dissolved in 25 ml of 2-chloroethanol 5 ml of sulfuric acid was added dropwise and continued heating at 90° C. for 24 h. Excess acid and 2-chloroethanol were removed under vacuum and the residue was extracted with ethylacetate. Organic layer was washed with water, brine and dried over anh.sodium sulfate. Concentration of the solvent afforded 1.2 g of brownish solid Step 2: The above solid was purified by column chromatography to afford 650 mg of 5-(2'-chloroethoxy) camptothecin of the formula 1 and 150 mg of previously prepared 5-hydroxy-camptothecin of the formula 13 where R$^1$=R$^2$=R$^3$=R$^4$=R$^5$=H; mp: 202° C.; [α]$_D$ at 28° C.=+5.37 (c 0.093, CHCl$_3$); IR: 3354, 1744, 1662, 1622, 1223, 1160, 1090, 1044, 752, 663 cm$^{-1}$; Partial $^1$H NMR data in CDCl$_3$: δ 6.92 (s, 0.5H), 6.82(s, 0.5H), 4.51(t, J=5 Hz, 1.5H), 4.38(t, J=5 Hz, 1.5H), 3.75(s, 1H, D$_2$O exchangeable), 3.85–3.58(m, 2H), 2.00–1.78(m, 2H), 1.06(t, J=7.5 Hz, 3H); Mass(m/z): 426(M+1), 391, 377, 363, 348, 319, 105, 84, 51.

Example 25

Preparation of 5-trifluoroethoxycamptothecin of the formula 1 where R$^1$=R$^2$=R$^3$=R$^4$=R$^5$=H, R$^6$=CH$_2$CF$_3$ Step 1: To a mixture of 20(S)-Camptothecin of the formula 3 (0.5 g), ferric chloride (0.5 g), dissolved in 18 ml of 2,2,2-trifluoroethanol, sulfuric acid was added dropwise and continued heating at 80° C. for 24 h. Excess acid and trifluoroethanol were removed under vacuum and the residue was extracted with ethylacetate. Organic layer was washed with water, brine and dried over anh.sodium sulfate. Concentration of the solvent afforded 600 mg of solid material.

Step 2: The above solid material was purified by column chromatography to give 250 mg of 5-trifluoroethoxycamptothecin of the formula 1 along with 150 mg of previously prepared 5-hydroxycamptothecin of the formula 13; mp 188° C. ; IR: 3438, 1748, 1667, 1620, 1160, 1106, 1003 cm$^{-1}$; Partial $^1$H NMR data in CDCl$_3$: δ 6.84 (s, 0.5H), 6.75(s, 0.5H), 5.21–4.90(m, 1H), 4.60–4.38 (m,2H), 3.70(s, 1H, D$_2$O exchangeable), 2.0–1.79(m, 2H), 1.15–0.99(m, 3H); Mass (m/z):447 (M+1), 378, 348, 304, 111, 69.

Example 26

Preparation of 5-(2'-Hydroxyethoxy)camptothecin of the formula 1 where R$^1$=R$^2$=R$^3$=R$^4$=R$^5$=H, R$^6$=CH$_2$CH$_2$OH Step 1: To a mixture of 20(S)-Camptothecin of the formula 3 (1 g), ferric chloride (1 g), dissolved in 10 ml of ethylene glycol, 5 ml of sulfuric acid was added dropwise and continued heating at 70° C. for 36 h. Excess acid and ethylene glycol were removed under vacuum and the residue was extracted with ethylacetate. Organic layer was washed with water, brine and dried over anh.sodium sulfate. Concentration of the solvent gave 1.1 g of yellowish powder.

Step 2: The solid obtained as above was subjected to column purification using ethylacetate-hexane solvent mixture to afford 700 mg of 5-(2'-Hydroxyethoxy)camptothecin of the formula 1 and 200 mg of previously prepared 5-hydroxycamptothecin of the formula 13 where R$^1$=R$^2$=R$^3$=R$^4$=R$^5$=H; mp: 190° C.; [α]$_D$ at 26° C.=+28.30 (c 0.106, CHCl$_3$); IR: 3300, 3285, 1745, 1665, 1620, 1605, 1227, 1160, 1112, 1047 cm$^{-1}$; Partial $^1$H NMR data in CDCl$_3$: δ 7.01 (s, 0.5H), 6.92 (s, 0.5H), 4.30–3.71(m, 4H), 3.75(br s, 2H, D$_2$O exchangeable), 2.0–1.79(m 2H), 1.15–0.95 (m, 3H); Mass (m/z): 408(M+1), 390, 378, 364, 348, 319, 101, 76.

Example 27

Preparation of 10-Hydroxy-5-trifluoroethoxycamptothecin of the formula 1 where $R^1=R^3=R^4=R^5=H$, $R2=OH$, $R^6=CH_2CF_3$ Step 1: Initially 10,5-dihydroxycamptothecin of the formula 13 where $R^1=R^3=R^4=R^5=H$, $R^2=OH$, was prepared as described in the example 22.

Step 2: A mixture of 10,5-dihydroxycamptothecin of the formula 13 where $R^2=OH$, $R^1=R^3=R^4=R^5=H$ (200 mg) and trifluoroethanol (1 mL) were suspended in 50 ml of dichloroethane and heated to reflux in the presence of sulfuric acid (0.5 ml) for 18 h. Reaction mixture was concentrated to dryness and the residue was extracted with ethylacetate. Organic layer was washed with water and brine and dried over anh.sodium sulfate. Evaporation of the solvent furnished an oily residue which was purified over silica gel column using acetonechloroform as an eluent to get 140 mg of 10-Hydroxy-5-trifluoroethoxycamptothecin of the formula 1 as a solid; mp: 237° C.; IR: 3420, 1748, 1664, 1605, 1159 cm$^{-1}$; $^1$H NMR(DMSO-d6): δ 10.48(s, 1H, D$_2$O exchangeable), 8.45(s, 1H), 8.04(d, J=9 Hz, 1H), 7.47(d, J=9 Hz, 1H), 7.40(s, 1H), 7.18(s, 1H), 7.11(s, 0.5H), 7.06(s, 0.5H), 6.58(s, 1H, D$_2$O exchangeable), 5.41(s,2H), 5.05–4.55(m, 2H), 2.05–1.75(m,2H), 1.00–0.8(m,3H); $^{13}$C NMR (DMSO-d6): δ 172.4, 161.0, 157.7, 157.1, 151.2, 147.5, 144.3, 143.7, 131.0, 130.8, 129.8, 129.1, 124.0, 121.4, 120.7, 109.6, 96.6, 89.7, 72.3, 65.1, 30.4, 7.8: Mass (m/z): 462(M+1), 418, 364, 320, 291, 263.

Example 28

Preparation of 9-Nitro-5-trifluoroethoxycamptothecin of the formula 1 where $R^2=R^3=R^4=R^5=H$, $R^1=NO_2$ $R^6=CH_2CF_3$ Step 1: Initially 9-nitro-5-hydroxycamptothecin of the formula 13 where $R^2=R^3=R^4=R^5=H$, $R^1=NO_2$ was prepared as described in the example 21.

Step 2: A mixture of 9-nitro-5-dihydroxycamptothecin of the formula 13 where $R^1=NO_2$, $R^2=R^3=R^4=R^5=H$ (100 mg) and trifluoroethanol (0.5 mL) were suspended in 25 ml of dichloroethane and heated to reflux in the presence of sulfuric acid (0.3 ml) for 18 h. Reaction mixture was concentrated to dryness and the residue was extracted with ethylacetate. Organic layer was washed with water and brine and dried over anh.sodium sulfate. Evaporation of the solvent furnished an oily residue which was purified over silica gel column using acetone-chloroform as an eluent to get 60 mg of 9-nitro-5-trifluoroethoxycamptothecin of the formula 1 as a solid.; mp 210° C.; IR: 3457, 1745, 1665, 1623, 1527, 1154, 1000 cm$^{-1}$; $^1$H NMR (CDCl$_3$): δ 9.30(s, 1H), 8.53(d, J=8.6 Hz, 1H), 8.49(d, J=8.6 Hz, 1H), 7.94(t, J=8 Hz, 1H), 7.62(s, 0.5H), 7.60(s, 0.5H), 6.87(s, 0.5H), 6.81(s, 0.5H), 5.69(d, J=16 Hz, 1H), 5.29(d, J=16 Hz, 1H), 4.97(m, 1H), 4.52(m, 1H), 3.90(br s, 1H, D$_2$O exchangeable), 1.90(m, 2H), 1.05(t, J=7 Hz, 3H); Mass (m/z): 491(M+1), 461, 446, 418, 393, 364, 349, 319, 290, 216

Example 29

Preparation of 5-(2'-fluoroethoxy) camptothecin of the formula 1 where $R^1=R^2=R^3=R^4=R^5=H$, $R^6=CH_2CH_2F$ Step 1: Initially 5-hydroxycamptothecin of the formula 13 where $R^1=R^2=R^3=R^4=R^5=H$, was prepared as described in the example 2.

Step 2: A mixture of 5-hydroxycamptothecin of the formula 13 where $R^1=R^2=R^3=R^4=R^5=H$ (200 mg) and 2-fluoroethanol (2mL) were suspended in 30 ml of dichloroethane and heated to reflux in the presence of sulfuric acid (0.3 ml) for 18 h. Reaction mixture was concentrated to dryness and the residue was extracted with ethylacetate. Organic layer was washed with water and brine and dried over anh.sodium sulfate. Evaporation of the solvent furnished an oily residue which was purified over silica gel column using acetone-chloroform as an eluent to get 130 mg of 5-(2'-fluoroethoxy)camptothecin of the formula 1 as a solid; mp: 174° C.; IR: 1745, 1664, 1615, 1160, 1040, 752 cm$^{-1}$; $^1$N NMR (CDCl$_3$+DMSO-d6): δ 8.46(s, 1H), 8.20(d, J=8 Hz, 1H), 7.95(d, J=8 Hz, 1H), 7.83 (t, 3=6.8 Hz, 1H), 7.65–7.55(m, 2H), 6.86(s, 0.5H), 6.78(s, 0.5H), 5.68(d, J=16.5 Hz, 1H), 5.26(d, J=16.5 Hz, 1H), 4.90–4.20 (m, 4H), 4.44(s, 1H, D$_2$O exchangeable), 2.05–1.85(m, 2H), 1.12–0.95(m, 3H) ; Mass(m/z): 410(M+1), 365, 348, 319, 304.

Example 30

Preparation of 10-Hydroxy-5-(2'-fluoroethoxy) camptothecin of the formula 1 where $R^1=R^3=R^4=R^5=H$, $R^2=OH$, $R^6=CH_2CH_2F$ Step 1: Initially 10,5-dihydroxycamptothecin of the formula 13 where $R^1=R^3=R^4=R^5=H$, $R^2=OH$, was prepared as described in the example 22.

Step 2: A mixture of 10,5-dihydroxycamptothecin of the formula 13 where $R^2=OH$, $R^1=R^3=R^4=R^5=H$ (100 mg) and 2-fluoroethanol (2 mL) were suspended in 25 ml of dichloroethane and heated to reflux in the presence of sulfuric acid (0.2 ml) for 16 h. Reaction mixture was concentrated to dryness and the residue was extracted with ethylacetate. Organic layer was washed with water and brine and dried over anh.sodium sulfate. Evaporation of the solvent furnished an oily residue which was purified over silica gel column using acetone-chloroform as an eluent to get 60 mg of 10-Hydroxy-5-fluoroethoxycamptothecin of the formula 1 as a solid; mp: 258–260° C.; IR: 3225, 1748, 1660, 1593, 1159 cm$^{-1}$; $^1$H NMR (CDCl$_3$+DMSO-d6): δ 10.0 (br s, 1H, D$_2$O exchangeable), 8.31(s, 1H), 8.00(d, J=6 Hz, 1H), 7.80(s, 1H), 7.45(d, J=6 Hz, 1H), 7.40(s, 1H), 6.85(s, 0.5H), 6.80(s, 0.5H), 6.15(s, 1H, D$_2$O exchangeable), 5.55(d, J=16 Hz, 1H), 5.23(d, J=16 Hz, 1H), 4.85–4.20(m, 4H), 2.05–1.81 (m,2H), 1.0(t, J=7 Hz, 3H); Mass(m/z): 426(M+1), 382, 364, 320.

Example 31

Preparation of 5-(2'-Fluoroethoxy)-7-ethylcamptothecin

Step 1: Initially 5-hydroxy-7-ethylcamptothecin of the formula 13 where $R^1=R^2=R^3=R^4=H$, $R^5=Et$, was prepared as described in the example 4.

Step 2: To a mixture of 80 mg of 5-hydroxy-7-ethylcamptothecin and 0.1 ml of p-toluenesulfonic acid suspended in 12 ml of benzene, 20 mg of 2-fluoroethanol was added and heated the mixture to reflux temperature for 14 h. Reaction was quenched with a drop of pyridine and extracted with ethyl acetate. Organic layer was washed with water, NaHCO$_3$, brine and concentrated to dryness. The residue was purified by silica gel column chromatography using ethyl acetate-chloroform as eluent to afford 60 mg of 5-(2'-fluoroethoxy)-7-ethylcamptothecin; mp: 112° C.; IR: 3070, 1748, 1665, 1605, 1456, 1155, 1038, 767 cm$^{-1}$; $^1$H NMR (CDCl$_3$): δ 8.21 (d, J=9.2 Hz, 1H), 8.17(d, J=9.2 Hz, 1H), 7.82(t, J=7.4 Hz, 1h), 7.67(t, J=7.4 Hz, 1H), 7.57(s, 0.5H), 7.54(s, 0.5H), 7.00(s, 0.5H), 6.89(s, 0.5H), 5.69(d, J=16 Hz, 1H), 5.27(d, J=16 Hz, 1H), 4.81–4.12(m, 4H), 3.51–3.15(m, 2H), 1.93(m, 2H), 1.45(t, J=7 Hz, 3H), 1.05 (m, 3H); Mass (m/z): 438(M+1), 420, 406, 376, 347, 332, 317, 245, 91.

Example 32

Preparation of 5-(2'-Hydroxyethoxy)-7-ethylcamptothecin

Step 1: Initially 5-hydroxy-7-ethylcamptothecin of the formula 13 where $R^1=R^2=R^3=R^4=H$, $R^5=Et$, was prepared as described in the example 4.

Step 2: To a mixture of 250 mg of 5-hydroxy-7-ethylcamptothecin and 10 μl of conc.sulfuric acid suspended in 25 ml of dichloroethane, 0.5 ml of ethylene glycol was added and heated the mixture to reflux temperature for 14 h. Reaction was quenched with a drop of pyridine and extracted with ethyl acetate. Organic layer was washed with water and brine and concentrated to dryness. The residue was purified by silica gel column chromatography using ethyl acetate-chloroform as eluent to furnish 180 mg of 5-(2'-hydroxyethoxy)-7-ethylcamptothecin and 25 mg of starting material; $^1$H NMR (CDCl$_3$, 200 MHz): δ 8.20(d, J=8 Hz, 1H), 8.15(d, J=8 Hz, 1H), 7.85(t, J=6.8 Hz, 1H), 7.69(t, 7.3 Hz, 1H), 7.56(s, 0.5H), 7.54(s, 0.5H), 7.11(s, 0.5H), 6.99(s, 0.5H), 5.72(d, J=16.5 Hz, 1H), 5.28(d, J=16.5 Hz, 0.5H), 5.26(d, J=16.5 Hz, 0.5H), 3.95–3.65(m, 4H), 3.78 (br s, 2H, D$_2$O exchangeable), 3.5–3.18 (m, 2H), 1.95–1.81(m, 2H), 1.45(t, J=7.5 Hz, 3H), 1.06(m, 3H).

Example 33

Preparation of 5-(2'-Hydroxyethoxy)-10-hydroxycamptothecin

Step 1: Initially 10,5-dihydroxycamptothecin of the formula 13 where $R^1=R^3=R^4=R^5=H$, $R^2=OH$, was prepared as described in the example 22.

Step 2: To a mixture of 60 mg of 10,5-dihydroxycamptothecin and 5 mg of p-toluenesulfonic acid suspended in 10 ml of dichloroethane, 25 mg of ethylene glycol was added and heated the mixture to reflux temperature for 16 h. Reaction was quenched with a drop of pyridine and extracted with ethyl acetate. Organic layer was washed with water and brine and concentrated to dryness. The residue was purified by silica gel column chromatography using methanol-chloroform as eluent to furnish 40 mg of 5-(2'-hydroxyethoxy)-10-hydroxycamptothecin and 10 mg of starting material; IR; 3070, 1760, 1660, 1600, 1558, 1509, 1384, 1160, 1047, 832 cm$^{-1}$; $^1$H NMR CDCl$_3$+DMSO): δ 10.05(br, 1H D$_2$O exchangeable), 8.35(s, 1H), 8.05(d, J=9 Hz, 1H), 7.75(s, 1H), 7.45(d, J=9 Hz, 1H), 7.28(s, 1H), 6.95(s, 0.5H), 6.85(s, 0.5H), 5.65(d, J=16 Hz, 1H), 5.25(d, J=16 Hz, 1H), 4.11(m, 2H), 3.78(m, 2H), 4.05(br s, 1H, D$_2$O exchangeable), 1.98(m, 2H), 1.05(t, J=7 Hz, 3H); Mass (m/z): 425, 408, 380, 364, 336, 320, 305, 264, 235, 147, 105.

Example 34

Preparation of 5,10-Dihydroxy-7-ethylcamptothecin

Step 1: Initially 5-ethoxy-10-hydroxy-7-ethylcamptothecin of the formula 1 where $R^1=R^3=R^4=H$, $R^5=R^6=Et$, $R^2=OH$ was prepared as described in the Example 18.

Step 2: 12 ml of 25%HCl was added to 200 mg of 5-ethoxy-10-hydroxy-7-ethylcamptothecin dissolved in 10 ml of ethanol and heated to reflux for 24 h. Excess acid and ethanol were distilled off and the remaining residue was diluted with ethylacetate. The organic layer was washed with 5% NaHCO$_3$ solution and brine. Concentration of the solvent and purification of the solid material over silica gel column using acetone-chloroform solvent mixture as eluent afforded 105 mg of 5,10-dihydroxy-7-ethylcamptothecin; mp: 197° C.; IR: 3268, 2975, 1748, 1656, 1597, 1514, 1230, 1161, 1052, 841 cm$^{-1}$; $^1$H NMR (CDCl$_3$+DMSO): δ 10.0(br s, 1H, D$_2$O exchangeable), 8.05(d, J=9 Hz, 1H), 7.76(s, 2H), 7.42(m, 1H), 7.04(s, 0.51), 6.98(s, 0.5H), 5.65(d, J16 Hz, 1H), 5.23(d, J=16 Hz, 1H), 3.51(br s, 1H, D$_2$O exchangeable), 3.45–3.12(m, 21), 1.94(m, 2H), 1.42(t, J=7 Hz, 3H), 1.01(t, J=7 Hz, 3H); Mass(m/z): 408(M+1), 379, 364, 347, 335, 285, 169, 119, 101, 83.

Example 35

Preparation of 5-(2'Hydroxyethoxy)-10-hydroxy-7-ethylcamptothecin

Step 1: Initially 7-ethyl-5,10-dihydroxy camptothecin of the formula 13 where $R^1=R^3=R^4=H$, $R^2=OH$, $R^5=Et$, was prepared as described in the example 34.

Step 2: To a mixture of 100 mg of 10,5-dihydroxy-7-ethylcamptothecin and 5 mg of p-toluenesulfonic acid suspended in 10 ml of dichloroethane, 50 mg of ethylene glycol was added and heated the mixture to reflux temperature for 16 h. Reaction was quenched with a drop of pyridine and extracted with ethyl acetate. Organic layer was washed with water and brine and concentrated to dryness. The residue was purified by silica gel column chromatography using methanolchloroform as eluent to furnish 60 mg of 5-(2'-hydroxyethoxy)-10-hydroxy-7-ethylcamptothecin and 12 mg of starting material.; mp: 124° C.; $^1$H NMR (CDCl$_3$+DMSO): δ 10.0 (br s, 1H, D$_2$O exchangeable), 8.02(d, J=9 Hz, 1H), 7.55–7.39(m, 3H), 7.02(s, 0.5H), 6.93(s, 0.5H), 6.05 (br s, 1H, D$_2$O exchangeable), 5.63(d, J=16 Hz, 1H), 5.23(d, J=16 Hz, 1H), 3.94–3.54(m,2H), 3.41–3.05(m 2H), 1.93(m,2H), 1.40(t, J=7 Hz,3H), 1.02(m,3H); Mass (m/z): 408(M+1), 379, 364, 347, 335, 285, 169, 119, 101, 83.

Example 36

Preparation of 5-(2'-aminoethoxy) camptothecin

Step 1: Initially 5-hydroxy camptothecin of the formula 13 where $R^1=R^2=R^3=R^4=R^5=H$, was prepared as described in the example 2.

Step 2: To a mixture of 60 mg of 5-hydroxycamptothecin and 5 mg of p-toluenesulfonic acid suspended in 10 ml of benzene, 15 mg of 2-aminoethanol was added and heated the cure to reflux temperature for 14 h. Reaction was quenched with a drop of pyridine and extracted with ethyl acetate. Organic layer was washed with water, NaHCO$_3$, brine and concentrated to dryness. The residue was purified by silica gel column chromatography using methanolchloroform as eluent to furnish 36 mg of 5-(2'-aminoethoxy)camptothecin and 10 mg of starting material; mp: 170° C.; IR: 3451, 1740, 1664, 1604, 1383, 1189, 1042 cm$^{-1}$; Partial $^1$H NMR data in (CDCl$_3$+DMSO-d6): δ 7.5 (d, D$_2$O exchangeable, 1H), 7.15(d, D$_2$O exchangeable, 1H), 7.02 (s, 0.5H), 6.92(s, 0.5H), 5.65(d, J=16 Hz, 1H), 5.28(d, J=16 Hz, 1H), 4.24–3.85(m, 2H), 2.35(s, D$_2$O exchangeable, 1H), 2.34(m, 1H), 2.15–1.85(m, 3H), 1.12–0.95(m, 3H); Mass (m/z): 408(M+1), 364, 347, 319, 305, 291, 249, 103, 62.

Example 37

Preparation of 5-(2'-aminoethoxy)-7-ethylcamptothecin

Step 1: Initially 5-hydroxy-7-ethylcamptothecin of the formula 13 where $R^1=R^2=R^3=R^4=H$, $R^5=Et$, was prepared as described in the example 4.

Step 2: To a mixture of 85 mg of 7-ethyl-5-hydroxycamptothecin and 5 mg of p-toluenesulfonic acid suspended in 20 ml of benzene, 11 mg of 2-aminoethanol was added and heated the mixture to reflux temperature for 10 h. Reaction was quenched with a drop of pyridine and extracted with ethyl acetate. Organic layer was washed with water, $NaHCO_3$, brine and concentrated to dryness. The residue was purified by silica gel column chromatography using methanol-chloroform as eluent to afford 65 mg of 5-(2'-aminoethoxy)-7-ethylcamptothecin. mp: 230° C.; Partial $^1H$ NMR in ($CDCl_3+DMSO-d6$): δ 7.5(d, $D_2O$ exchangeable, 1H), 7.15(d, $D_2O$ exchangeable, 1H), 7.02(s, 0.5H), 6.92(s, 0.5H), 5.65(d, J=16 Hz, 1H), 5.28(d, J=16 Hz, 1H), 4.24–3.85(m, 2H), 2.35(s, $D_2O$ exchangeable, 1H), 2.34(m, 1H), 2.15–1.85(m, 3H), 1.12–0.95(m, 1H); Mass (m/z): 408(M+1), 364, 347, 319, 305, 103, 74, 62.

Example 38

Preparation of 5-(3'-dimethylaminopropoxy)-7-ethylcamptothecin

Step 1: Initially 5-hydroxy-7-ethylcamptothecin of the formula 13 where $R^1=R^2=R^3=R^4=H$, $R^5=Et$, was prepared as described in the example 4.

Step 2: To a mixture of 50 mg of 7-ethyl-5-hydroxycamptothecin and 0.05 ml of sulfuric acid suspended in 20 ml of benzene, 30 mg of 3-dimethylamino-1-propanol was added and heated the mixture to reflux temperature for 12 h. Reaction was quenched with a drop of pyridine and extracted with ethyl acetate. Organic layer was washed with water, $NaHCO_3$, brine and concentrated to dryness. The residue was purified by silica gel column chromatography using methanol-chloroform as eluent to obtain 42 mg of 5-(3'-dimethylaminopropoxy)-7-ethylcamptothecin; mp: 113° C.; Partial $^1H$ NMR data in ($CDCl_3+DMSO-d6$): δ 6.95 (s, 0.5H), 6.85(s, 0.5H), 5.65(d, J=16 Hz, 1H), 5.35(d, J=16 Hz, 0.5H), 5.25(d, J=16 Hz, 0.5H), 3.95–3.57(m, 2H), 3.30–3.05(m, 2H), 2.85(s, 3H), 2.83(s, 3H), 2.15–1.72(m, 6H), 1.45(t, J=7.5 Hz, 3H), 1.12–0.95(m, 3H); Mass (m/z): 478(M+1), 434, 375, 347, 331, 169, 102, 84; Mass(m/z): 478(M+1), 434, 375, 347, 331, 169, 102, 84.

Example 39

Preparation of 5-(2'-N-pyrrolidinoethoxy)-7-ethylcamptothecin

Step 1: Initially 5-hydroxy-7-ethylcamptothecin of the formula 13 where $R^1=R^2=R^3=R^4=H$, $R^5=Et$, was prepared as described in the example 4.

Step 2: To a mixture of 100 mg of 7-ethyl-5-hydroxycamptothecin and 10 mg of camphorsulfonic acid suspended in 25 ml of benzene, 30 mg of 1-(2-hydroxyethyl) pyrrolidine was added and heated the mixture to reflux temperature for 16 h. Reaction was quenched with a drop of pyridine and extracted with ethyl acetate. Organic layer was washed with water, $NaHCO_3$, brine and concentrated to dryness. The residue was purified by silica gel column chromatography using methanol-chloroform as eluent to acetate 85 mg of 5-(2'-N-pyrrolidinoethoxy)-7-ethylcamptothecin; mp: 225° C.; IR: 3424, 1749, 1666, 1616, 1384, 1156, 1078, 1049 cm−1; Partial $^1H$ NMR data in $CDCl_3$: d 7.02 (s, 0.5H), 6.95(s, 0.5H), 5.70(d, J=16 Hz, 1H), 5.33(d, J=16 Hz, 0.5H), 5.26(d, J=16 Hz, 0.5H), 4.18–3.88(m, 2H), 3.45–3.15(m,2H), 3.06–2.58(m, 6H), 2.05–1.72(m, 6H), 1.43(t, J=8 Hz, 3H), 1.15–0.95(m,3H); Mass (m/z): 446 (M+1), 375, 347, 331, 245, 169, 116, 97, 84.

Example 40

Preparation of 5-(2'-chloroethoxy)-7-ethylcamptothecin

Step 1: Initially 5-hydroxy-7-ethylcamptothecin of the formula 13 where $R^1=R^2=R^3=R^4=H$, $R^5=Et$, was prepared as described in the example 4.

Step 2: To a mixture of 500 mg of 7-ethyl-5-hydroxycamptothecin and 0.1 ml of conc.sulfuric acid suspended in 30 ml of benzene, 700 mg of 2-chloroethanol was added and heated the mixture to reflux temperature using Dean-Stork apparatus for 8 h. Reaction was quenched with a drop of pyridine and extracted with ethyl acetate. Organic layer was washed with water, $NaHCO_3$, brine and concentrated to dryness. The residue was purified by silica gel column chromatography using ethyl acetate-chloroform as eluent to provide 400 mg of 5-(2'-chloroethoxy)-7-ethylcamptothecin; mp: 168° C.; $^1H$ NMR ($CDCl_3$, 200 MHz): δ 8.20(d, J=9.5 Hz, 1H), 8.15(d, J=9.5 Hz, 1H), 7.82(t, J=8 Hz, 1H), 7.67(t, J=8 Hz, 1H), 7.54(d, 6.2 Hz, 1H), 7.02(s, 0.5H), 6.90(s, 0. 5H), 5.70(d, J=16 Hz, 0.5H), 5.69(d, J=16 Hz, 0.5H), 5.26(d, J=16 Hz, 0.5H), 5.25(d, J=16 Hz, 0.5H), 4.61–3.95(m, 2H), 3.78–3.58(m, 2H), 3.50–3.15(m, 2H), 1.98–1.78(m, 2H), 1.45-(t, 3=7.5 Hz, 3H), 1.12–0.95(m, 3H); Mass (m/z): 455(M+1), 437, 409, 392, 376, 347, 331, 245, 115, 81.

Example 41

Preparation of 5-(2'-dimethylaminoethoxy)-7-ethylcamptothecin

Step 1: Initially 5-hydroxy-7-ethylcamptothecin of the formula 13 where $R^1=R^2=R^3=R^4=H$, $R^5=Et$, was prepared as described in the example 4.

Step 2: To a mixture of 100 mg of 7-ethyl-5-hydroxycamptothecin and 0.1 ml of conc.sulfuric acid suspended in 10 ml of benzene, 50 mg of 2-N,N-dimethylaminoethanol was added and heated the mixture to reflux temperature using Dean-Stark apparatus for 10 h. Reaction was quenched with a drop of pyridine and extracted with ethyl acetate. Organic layer was washed with water, $NaHCO_3$, brine and concentrated to dryness. The residue was purified by silica gel column chromatography using methanol-chloroform as eluent to get 65 mg of 5-(2'-dimethylaminoethoxy)-7-ethylcamptothecin; Partial $^1H$ NMR data in $CDCl_3$: δ 7.05 (s, 0.5H), 6.93(s, 0.5H), 5.74(d, J=16 Hz, 0.5H), 5.73(d, J=16 Hz, 0.5H), 5.29(d, J=16 Hz, 1H), 4.41–3.75(m, 2H), 3.53–3.18(m, 2H), 2.57(q, J=6 Hz, 2H), 2.26(s, 3H), 2.23(s, 3H), 2.05–1.86(m, 2H), 1.47(t, J=8 Hz, 3H), 1.18–1.01(m, 3H).

Example 42

Preparation of 5-(4'-aminobutoxy)camptothecin

Step 1: Initially 5-hydroxy camptothecin of the formula 13 where $R^1=R^2=R^3=R^4=R^5=H$, was prepared as described in the example 2.

37

Step 2: To a mixture of 53 mg of 5-hydroxycamptothecin and 8 mg of p-toluenesulfonic acid suspended in 16 ml of benzene, 14 mg of 4-aminobutanol was added and heated the mixture to reflux temperature for 10 h. Reaction was quenched with a drop of pyridine and extracted with ethyl acetate. Organic layer was washed with water, NaHCO$_3$, brine and concentrated to dryness. The residue was purified by silica gel column chromatography using ethyl acetate-chloroform as eluent to furnish 45 mg of 5-(4-aminobutoxy) camptothecin; mp: 150° C.: IR: 3397, 1745, 1664, 1617, 1384, 1224, 1162, 1038, 684, 570 cm$^{-1}$; Partial $^1$H NMR data in (CDCl$_3$+DMSO-d6): δ 7.50(d, D$_2$O exchangeable, 1H), 6.95(s, 0.5H), 6.85(s, 0.5H), 6.25(d, D$_2$O exchangeable, 1H), 5.65(d, J=16 Hz, 1H), 5.35(d, J=16 Hz, 0.5H), 5.25(d, J=16 Hz, 0.5H), 4.15–3.80(m, 2H), 2.15–1.65(m, 8H), 1.15–0.98(m, 3H); Mass (m/z): 436(M+1), 392, 347, 333, 305, 153, 123, 105, 90, 62;

Example 43

Preparation of 5-(2'-methoxyethoxy)camptothecin

Step 1: Initially 5-hydroxy camptothecin of the formula 13 where R$^1$=R$^2$=R$^3$=R$^4$=R$^5$=H, was prepared as described in the example 2.

Step 2: To a mixture of 120 mg of 5-hydroxycamptothecin and 0.13 ml of sulfuric acid suspended in 18 ml of chloroform, 20 mg of ethyleneglycol monomethylether was added and heated the mixture to reflux temperature for 10 h. Reaction was quenched with a drop of pyridine and extracted with ethyl acetate. Organic layer was washed with water, NaHCO$_3$, brine and concentrated to dryness. The residue was purified by silica gel column chromatography using ethyl acetate-chloroform as eluent to furnish 80 mg of 5-(2'-methoxyethoxy)camptothecin; mp: 123° C.; IR, 3294, 2933, 1748, 1665, 1617, 1384, 1155, 1077, 1045, 761 cm$^{-1}$; $^1$H NMR (CDCl$_3$): δ 8.51(s, 1H), 8.24(d, J=8 Hz, 1H), 7.93(d, J=8 Hz, 1H), 7.79(t, J=6.8 Hz, 1H), 7.65(t, J=6.8 Hz, 1H), 7.58(s, 0.5H), 7.56(s, 0.5H), 6.91(s, 0.5H), 6.82(s, 0.5H), 5.71(d, J=16 Hz, 1H), 5.28(d, J=16 Hz, 1H), 4.55–4.05(m,2H), 3.95(br s, 1H, D$_2$O exchangeable), 3.81–3.56(m,2H), 3.48(s, 1.5H), 3.44(s, 1.5H), 1.94 (m,2H), 1.05(t, J=7 Hz, 3H); Mass(m/z): 423(M+1), 364, 347, 319, 304, 275, 218, 128, 101, 82.

Example 44

Preparation of 5-(2'N-Methylpyrrolidinoethoxy)-7-ethylcamptothecin

Step 1: Initially 5-hydroxy-7-ethylcamptothecin of the formula 13 where R$^1$=R$^2$=R$^3$=R$^4$=H, R$^5$=Et, was prepared as described in the example 4.

Step 2: To a mixture of 50 mg of 5-hydroxy-7-ethylcamptothecin and 10 mg of p-toluenesulfonic acid suspended in 15 ml of benzene, 18 mg of 1-methyl-2-pyrrolidinoethanol was added and heated the mixture to reflux temperature for 8 h. Reaction was quenched with a drop of pyridine and extracted with ethyl acetate. Organic layer was washed with water, NaHCO$_3$, brine and concentrated to dryness. The residue was purified by silica gel column chromatography using methanol-chloroform as eluent to furnish 35 mg of 5-(2'-N-Methylpyrrolidinoethoxy)-7-ethylcamptothecin; mp: 102° C.: Mass (m/z): 504(M+1), 460, 375, 347, 331, 275, 245, 128, 110, 84.

38

What is claimed is:
1. A compound of formula 1,

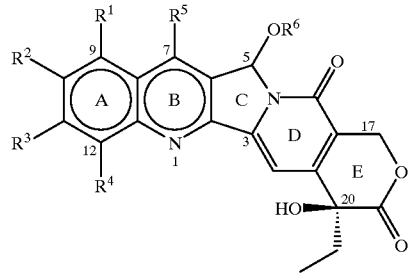

wherein

R$^1$, R$^2$, R$^3$ and R$^4$ independently represent hydrogen or represent a group selected from hydroxy, lower alkoxy, lower alkanoyl, nitro, cyano, halo, carboxy, amino, substituted amino wherein the amino group is mono or disubstituted and the substituents are selected from lower alkyl, lower haloalkyl, benzyl, benzoyl, carboxyl, amido or lower alkylamino; lower alkyl, or substituted lower alkyl wherein the substituents are selected from hydroxy lower haloalkyl, benzyl, lower alkoxy, benzyloxy, cyano, nitro, amino or lower alkylamino; or R$^2$ and R$^3$ together represent —O—(CH$_2$)$_n$—O— where n=1 or 2; each of R$^1$, R$^2$, R$^3$, and R$^4$ are not the same except where each of R$^1$, R$^2$, R$^3$, and R$^4$ are hydrogen;

R$^5$ represents hydrogen, lower alkyl, substituted lower alkyl, wherein the substituents are selected from hydroxy, halogen, lower alkoxy, benzyloxy, carboxy, amido, or amino where the amino group is mono or disubstituted and the substituents are selected from lower alkyl, lower haloalkyl, benzyl, or benzoyl, when the amino group is disubstituted the substituents are independent or together with the linking nitrogen atom form a saturated 5 or 6 membered heterocyclic ring of formula (A);

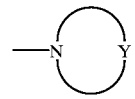
(A)

where Y represents O, S, NH or CH$_2$ when formula (A) is a 5-membered ring and Y represents CH$_2$ when formula (A) is a 6-membered ring; or R$^5$ represents lower aralkyl, where the aryl group is selected from phenyl, biphenyl or naphthyl; and R$^6$ represents phenyl or benzyl where the phenyl group may be unsubstituted or substituted with mono, di or trisubstituents selected from halogen, lower alkoxy, cyano, nitro, lower alkyl, amino, or substituted amino wherein the amino group is mono or disubstituted with lower alkyl groups; cycloalkyl or cycloalkyl lower alkyl where the cyclic ring has 3 to 7 ring atoms all of said ring atoms being carbon; lower alkyl groups substituted with saturated 5 or 6 membered heterocyclic ring of formula (B),

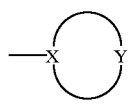
(B)

when formula (B) is a 5 membered ring X represents CH or N and Y represents O, S, NH or $CH_2$, when formula (B) is a 6 membered ring, X represents CH or N and Y represents $CH_2$; substituted benzoyl wherein the substituents are selected from lower alkyl, lower haloalkyl, halogen, lower alkoxy, thioalkoxy, cyano, nitro, amido, amino, or lower alkylamino; lower alkenyl, substituted lower alkyl, or substituted lower alkenyl, wherein the substituents are selected from halogen, hydroxy, lower alkoxy, aryloxy, thio, thioalkyl, thioaryl, aryl, wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro, amido or amino in which the amino group can be unsubstituted or mono, or disubstituted, wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

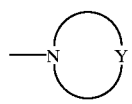
(A)

when formula (A) is a 5-membered ring, Y represents, O, S, NH or $CH_2$; when formula (A) is a 6-membered ring, Y represents $CH_2$;

or $R^6$ represents substituted lower alkanoyl wherein the substituents are selected from halogen, lower alkoxy, aryloxy, thio, thioalkyl, thioaryl, aryl, wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

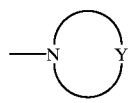
(A)

when formula (A) is a 5-membered ring, Y represents, O, S, NH or $CH_2$; when formula (A) represents a 6-membered ring Y represents $CH_2$; and when $R^1$ represents hydroxy, amino or nitro, $R^2$, $R^3$, $R^4$ and $R^5$ represent hydrogen and $R^6$ represents hydrogen, lower alkyl, alkanoyl or benzoyl groups.

2. A compound of the formula 1,

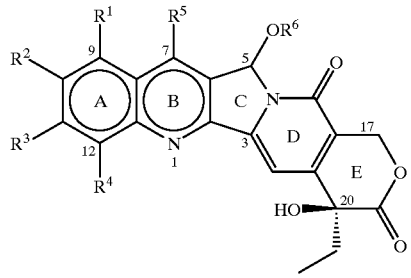

where $R^2$ represents hydroxy, $R^1$, $R^3$, $R^4$ and $R^5$ represent hydrogen, and $R^6$ represents trifluoroethyl group.

3. A compound of the formula 1,

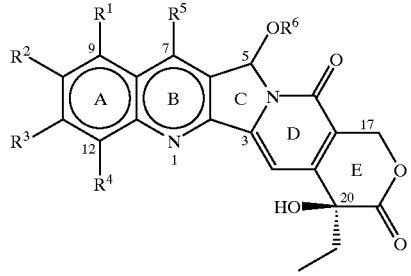

where $R^1$, $R^2$, $R^3$, $R^4$ and $R^5$ represent hydrogen, and $R^6$ represents fluoroethyl group.

4. A compound of the formula 1,

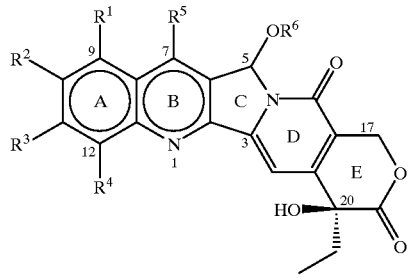

where $R^1$ represents N,N-dimethylaminomethyl, $R^2$ represents hydroxyl group, $R^3$, $R^4$ and $R^5$ represent hydrogen, and $R^6$ represents 2'-methoxyethyl group.

5. A compound of the formula 1,

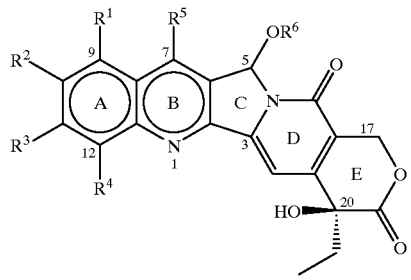

where $R^1$ represents nitro group, $R^2$, $R^3$, $R^4$ and $R^5$ represent hydrogen, and $R^6$ represents 2'-methoxyethyl group.

6. A compound of the formula 1,

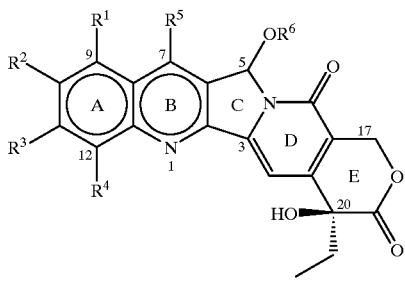

where $R^1$, $R^2$, $R^3$, $R^4$ and $R^5$ represent hydrogen, and $R^6$ represents 2'-hydroxyethyl group.

7. Compounds of the formula 1 where $R^1$ through $R^6$ have the meaning described in claim 1 as a mixture of two diastereomers, said diastereomers having 20(S),5(R) and 20(S),5(S), configurations.

8. A compound of the formula 1 having 20(S),5(R), configuration substantially free from the 20(S),5(S) stereoisomer where $R^1$ through $R^6$ have the meaning described in claim 1.

9. A pharmaceutical composition comprising an effective amount of a compound of formula 1 as defined in claim 1 or a pharmaceutically acceptable salt thereof and a pharmaceutically acceptable non-toxic excipient, diluent or solvent.

10. A process for the preparation of a compound of formula 1,

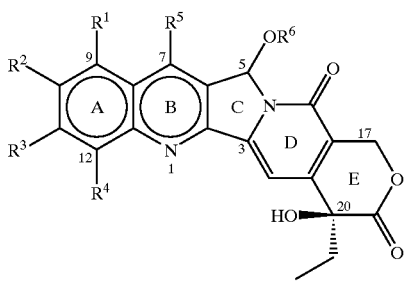

which comprises the steps of:
  (i) reacting a compound of formula 2,

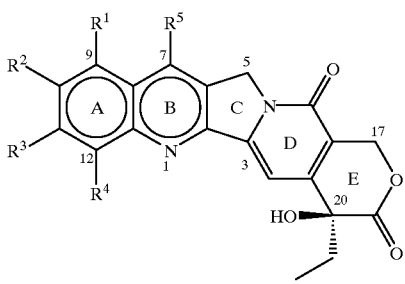

where $R^1$ to $R^5$ have meaning described in claim 1, in the presence of an acid, said acid selected from inorganic acid or Lewis acids and a ferric salt, with a compound having the formula $R^6$—OH where $R^6$ represents lower alkyl, lower alkenyl, ($C_3$–$C_7$)cycloalkyl, haloalkyl or hydroxyalkyl to obtain compounds of the formula 12 and compounds of the formula 13,

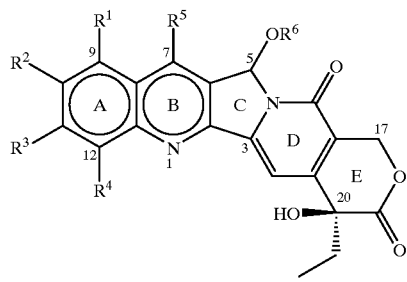

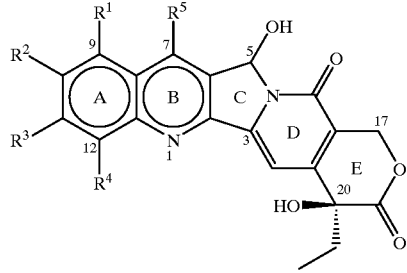

wherein $R^1$, $R^2$, $R^3$, $R^4$, and $R^5$ have the meaning described in claim 1, optionally;

(ii) separating the compounds of the formula 12 and 13 prepared in step (i), optionally;
  (iii) hydrolyzing the compounds of the formula 12 to obtain additional amounts of the compounds of the formula 13, and optionally,
  (iv) reacting the compound of the formula 13, in the presence of an acid, selected from inorganic acids, Lewis acids or organic acids with a compound having the formula $R^6$—OH to obtain compounds of formula 1,

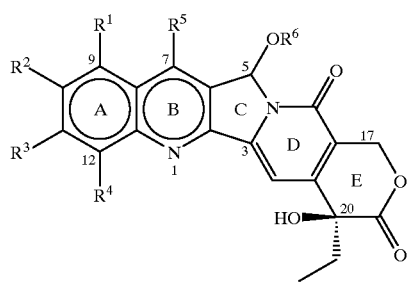

where $R^1$, $R^2$, $R^3$, $R^4$ and $R^5$ have the meaning described in claim 1 and $R^6$ represents phenyl or benzyl where the phenyl group may be unsubstituted or substituted with mono, di or trisubstituents selected from halogen, lower alkoxy, cyano, nitro, lower alkyl, amino, or substituted amino wherein the amino group is mono or disubstituted with lower alkyl groups; cycloalkyl or cycloalkyl lower alkyl where the cyclic ring has 3 to 7 ring atoms all of said ring atoms being carbon; lower alkyl groups substituted with saturated 5 or 6 membered heterocyclic ring of formula (B),

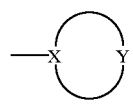

when formula (B) is a 5 membered ring, X represents CH or N and Y represents O, S, NH or CH$_2$; when formula (B) is a 6 membered ring, X represents CH or N and Y represents CH$_2$; substituted benzoyl wherein the substituents are selected from lower alkyl, lower haloalkyl, halogen, hydroxy, lower alkoxy, thioalkoxy, cyano, nitro, amido, amino, or lower alkylamino; lower alkenyl, substituted lower alkyl, or substituted lower alkenyl, wherein the substituents are selected from halogen, hydroxy, lower alkoxy, aryloxy, thio, thioalkyl, thioaryl, aryl, wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

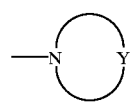

when formula (A) is a 5-membered ring, Y represents, O, S, NH or CH$_2$; when formula (A) is a 6-membered ring, Y represents CH$_2$; or R$^6$ represents substituted lower alkanoyl where the substituents are selected from halogen, lower alkoxy, aryloxy, thio, thioalkyl, thioaryl, aryl, wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

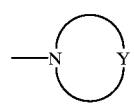

when formula (A) is a 5-membered ring, Y represents, O, S, NH or CH$_2$; when formula (A) represents a 6-membered ring, Y represents CH$_2$; and when R$^1$ represents hydroxy, amino or nitro, R$^2$, R$^3$, R$^4$ and R$^5$ represent hydrogen and R$^6$ represents hydrogen, lower alkyl, alkanoyl or benzoyl groups.

11. A process for the preparation of a compound of formula 1, where R$^1$, R$^3$, R$^4$ and R$^5$ are hydrogen, R$^2$ represents hydroxyl group and R$^6$ represents trifluoroethyl group, which comprises, the steps of:

(i) reacting the compound of formula 2,

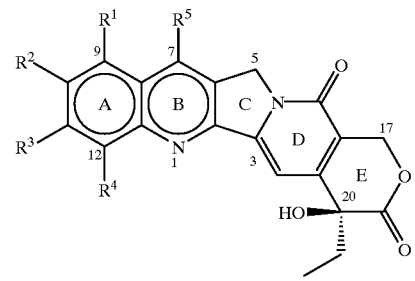

where R$^1$, R$^3$, R$^4$, and R$^5$ are hydrogen, R$^2$ represents hydroxyl group, in the presence of conc.sulfuric acid and ferric chloride trihydrate with ethanol and heating the mixture to reflux conditions to obtain compound of the formula 12 and compound of the formula 13,

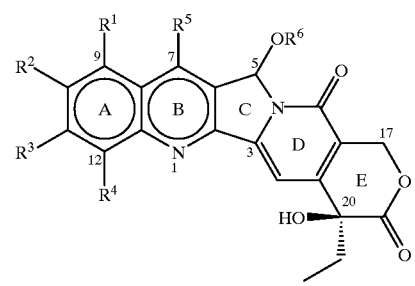

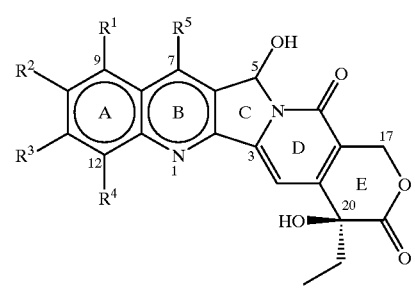

wherein R$^1$, R$^3$, R$^4$ and R$^5$ represent hydrogen, R$^2$ is hydroxyl group and R$^6$ represents ethyl group, (ii) separating the compounds of the formula 12 and 13 prepared in the step (i), (iii) hydrolyzing in compounds of the formula 12, by dissolving in aqueous ethanol and refluxing with hydrochloric acid, to obtain additional amounts of the compound of the formula 13, (iv) reacting the compound of the formula 13, in the presence of conc.sulfuric acid, with trifluoroethanol dissolved in dichloroethane solvent, to obtain the compound of the formula 1,

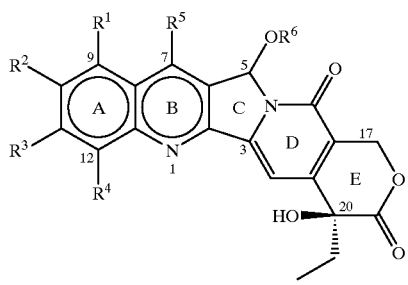

where $R^1$, $R^3$, $R^4$ and $R^5$ are hydrogen, $R^2$ represents hydroxyl group and $R^6$ represents trifluoroethyl group.

12. The process according to claim 10, wherein the ferric salt is ferric chloride.

13. A process for the preparation of a compound of formula 1,

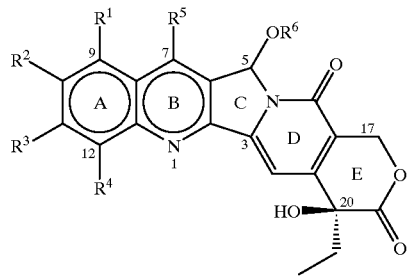

wherein $R^6$ represents hydrogen or lower alkyl, $R^1$ represents hydrogen or methoxy, $R^2$ represents hydrogen, hydroxy, lower alkoxy, acyloxy, SH, thioalkyl, thioacyl, nitro, amino, alkylamino, acylamino or halogen; $R^3$ and $R^4$ are hydrogen and $R^5$ represents hydrogen, lower alkyl, lower aralkyl wherein the aryl group is selected from phenyl, biphenyl or naphthyl; $CH_2OH$, COOH, COOMe or $CH_2OR''$ where $R''$ represents lower alkyl or acyl group which comprises, the steps of:

(i) reacting a compound of the formula 2,

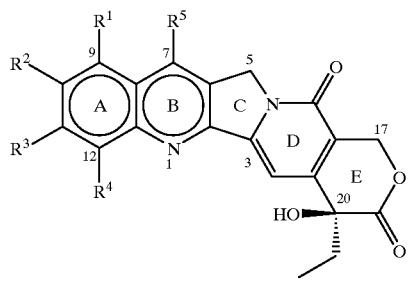

where $R^1$ to $R^5$ have the meaning described above, in the presence of an acid selected from inorganic acids, or Lewis acids and a ferric salt, with a compound of the formula $R^6$—OH where $R^6$ represents a lower alkyl group, to obtain compounds of formula 12 and compounds of formula 13,

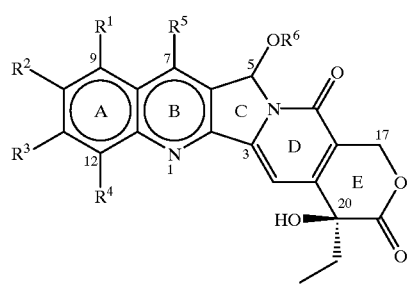

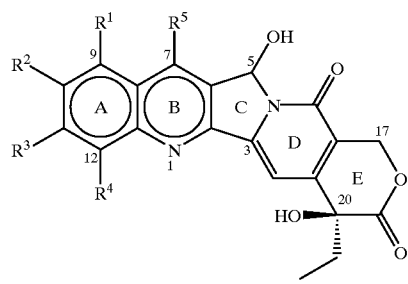

wherein $R^1$, $R^2$, $R^3$, $R^4$ and $R^5$ have the meaning given above, optionally (ii) hydrolyzing the compounds of the formula 12 to obtain additional amounts of the compounds of the formula 13, and optionally (iv) reacting the compound of the formula 13, in the presence of an acid, selected from organic acids, inorganic acids or Lewis acids, with a compound having the formula $R^6$—OH to obtain a compound of the formula 1,

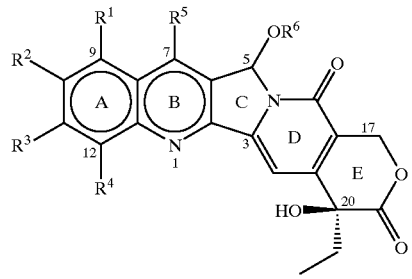

where $R^1$, $R^2$, $R^3$, $R^4$ and $R^5$ have the meaning described above, and $R^6$ represents lower alkyl group.

14. The process according to claim 13, wherein the ferric salt is ferric chloride.

15. A method of treating leukemia, lymphoma, non small cell lung cancer, cancer of the central nervous system, breast, colon, ovarian or renal cancer comprising administering to a patient in need of such treatment an effective amount of a compound of formula 1 as defined in claim 1.

16. A method of treating leukemia, lymphoma, non small cell lung cancer, cancer of the central nervous system, breast, colon, ovarian or renal patient in need of such treatment an effective amount of a compound of formula 1 as defined in claim 1 or a pharmaceutically acceptable salt thereof.

17. A compound selected from the group consisting of:
9-hydroxy-5-ethoxy CPT;
9-nitro-5-ethoxy CPT;

9-nitro-5-hydroxy CPT;
7-Ethyl-5-chloroethoxy CPT;
5-(2'-hydroxyethoxy) CPT;
10-hydroxy-5-(2'-hydroxyethoxy) CPT;
7-ethyl-10-hydroxy-5-(2'hydroxyethoxy) CPT;
9-nitro-5-fluoroethoxy CPT:
9-nitro-5-trifluoroethoxy CPT;
10-hydroxy-5-trifluoroethoxy CPT;
7-ethyl-10-hydroxy-5-trifluoroethoxy CPT;
7-ethyl-5-pyrrolidinoethoxy CPT;
7-ethyl-5-dimethylaminopropoxy CPT;
7-ethyl-10-hydroxy-5-fluoroethoxy CPT;
5-(2'-hydroxyethoxy)-7-ethyl CPT and
5-(2'-methoxyethoxy) CPT
where CPT represents 20(S)-camptothecin.

18. A compound of formula 1,

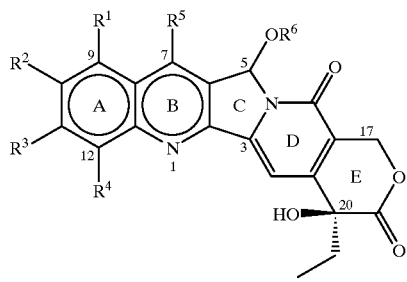

wherein $R^1$, $R^2$, $R^3$ and $R^4$ independently represent hydrogen or represent a group selected from hydroxy, lower alkoxy, lower alkanoyl, nitro, cyano, halo, carboxy, amino, substituted amino, wherein the amino group is mono or disubstituted and the substituents are selected from lower alkyl, lower haloalkyl, benzyl, benzoyl, carboxyl, amido, or lower alkylamino; lower alkyl, or substituted lower alkyl wherein the substituents are selected from hydroxy, lower haloalkyl, benzyl, lower alkoxy, benzyloxy, cyano, nitro, amino or lower alkylamino; or $R^2$ and $R^3$ together represent —O—(CH$_2$)$_n$—O— where n=1 or 2; each or $R^1$, $R^2$, $R^3$, and $R^4$ are not the same except where each of $R^1$, $R^2$, $R^3$ and $R^4$ are hydrogen;

$R^5$ represents hydrogen, lower alkyl, substituted lower alkyl, wherein the substituents are selected from hydroxy halogen, lower alkoxy, benzyloxy, carboxy, amido, or amino where the amino group is mono or disubstituted and the substituents are selected from lower alkyl, lower haloalkyl, benzyl, or benzoyl, when the amino group is disubstituted the substituents are independent or together with the linking nitrogen atom form a saturated 5 or 6 membered heterocyclic ring of formula (A);

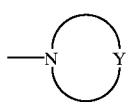

where Y represents O, S, NH or CH$_2$ when formula (A) is a 5-membered ring and Y represents CH$_2$ when formula (A) is a 6-membered ring; or $R^5$ represents lower aralkyl, wherein the aryl group is selected from phenyl, biphenyl or naphthyl; and $R^6$ represents phenyl or benzyl where the phenyl group may be unsubstituted or substituted with mono, di or trisubstituents selected from halogen, lower alkoxy, cyano, nitro, lower alkyl, amino, or substituted amino wherein the amino group is mono or disubstituted with lower alkyl groups; cycloalkyl or cycloalkyl lower alkyl where the cyclic ring has 3 to 7 ring atoms all of said ring atoms being carbon; lower alkyl groups substituted with saturated 5 or 6 membered heterocyclic ring of formula (B),

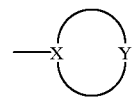

when formula (B) is a 5 membered ring X represents CH or N and Y represents O, S, NH or CH$_2$; when formula (B) is a 6 membered ring, X represents CH or N and Y represents CH$_2$; substituted benzoyl wherein the substituents are selected from lower alkyl, lower haloalkyl, halogen, lower alkoxy, thioalkoxy, cyano, nitro, amido, amino, or lower alkylamino; lower alkenyl, substituted lower alkyl, or substituted lower alkenyl, wherein the substituents are selected from halogen, hydroxy, lower alkoxy, aryloxy, thio, thioalkyl, thioaryl, aryl, wherein the aryl group is selected from phenyl, biphenyl; or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

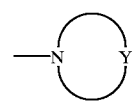

when formula (A) is a 5-membered ring, Y represents, O, S, NH or CH$_2$; when formula (A) is a 6-membered ring, Y represents CH$_2$; or $R^6$ represents substituted lower alkanoyl wherein the substituents are selected from halogen, lower alkoxy, aryloxy, thio, thioalkyl, thioaryl, aryl, wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

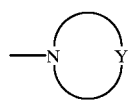
(A)

when formula (A) is a 5-membered ring, Y represents, O, S, NH or CH$_2$; when formula (A) is a 6-membered ring, Y represents CH$_2$; and when R$^1$ represents hydroxy, amino or nitro, R$^2$, R$^3$, R$^4$ and R$^5$ represent hydrogen and R$^6$ represents hydrogen, lower alkyl, alkanoyl or benzoyl groups prepared by the process comprising the steps of:

(i) reacting a compound of formula 2

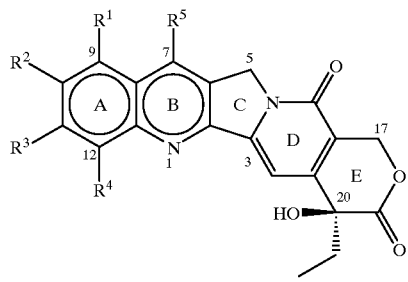

where R$^1$ to R$^5$ have the meaning described above, in the presence of acid said acid selected from inorganic acid or Lewis acids and a ferric salt, with a compound having the formula R$^6$—OH where R$^6$ represents lower alkyl, lower alkenyl, (C$_3$–C$_7$)cycloalkyl, haloalkyl or hydroxyalkyl to obtain compounds of the formula 12 and compounds of the formula 13,

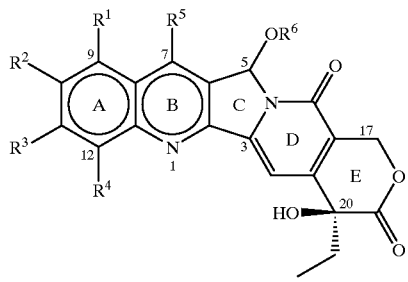

12

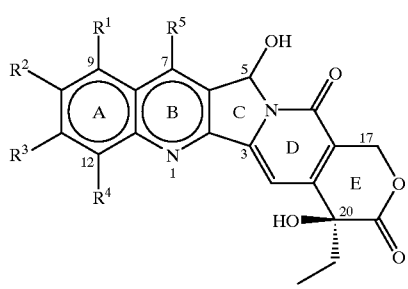

13 wherein R$^1$, R$^2$, R$^3$, R$^4$ and R$^5$ have the meaning given above, optionally;

(ii) separating the compounds of the formulas 12 and 13 prepared in step (i), optionally;

(iii) hydrolyzing the compounds of the formula 12 to obtain additional amounts of the compounds of the formula 13, and optionally;

(iv) reacting the compound of the formula 13, in the presence of an acid selected from inorganic acids, Lewis acids or organic acids, with a compound having the formula R$^6$—OH to obtain compounds of the formula 1,

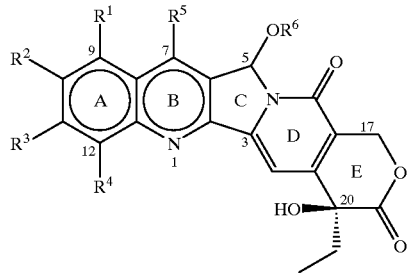

wherein R$^1$, R$^2$, R$^3$, R$^4$ and R$^5$ have the meaning described above;

R$^6$ represents phenyl or benzyl where the phenyl group may be unsubstituted or substituted with mono, di or trisubstituents selected from halogen, lower alkoxy, cyano, nitro, lower alkyl, amino, or substituted amino wherein the amino group is mono or disubstituted with lower alkyl groups; cycloalkyl or cycloalkyl lower alkyl where the cyclic ring has 3 t6 7 ring atoms all of said ring atoms being carbon; lower alkyl groups substituted with saturated 5 or 6 membered heterocyclic ring of formula (B),

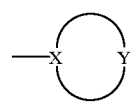
(B)

when formula (B) is a 5 membered ring X represents CH or N and Y represents O, S, NH or CH$_2$; when formula (B) is a 6 membered ring, X represents CH or N and Y represents CH$_2$; substituted benzoyl wherein the substituents are selected from lower alkyl, lower haloalkyl, halogen, lower alkoxy, thioalkoxy, cyano, nitro, amido, amino, or lower alkylamino; lower alkenyl, substituted lower alkyl, or substituted lower alkenyl wherein the substituents are selected from halogen, hydroxy, lower alkoxy, aryloxy, thio, thioalkyl, thioaryl, aryl, wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

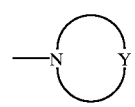
(A)

when formula (A) is a 5-membered ring, Y represents, O, S, NH or CH$_2$; when formula (A) represents a 6-membered ring, Y represents CH$_2$; or R⁶ represents substituted lower alkanoyl wherein the substituents are selected from halogen, lower alkoxy, aryloxy, thio, thioalkyl, thioaryl, aryl, wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

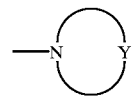

(A)

when formula (A) is a 5-membered ring, Y represents, O, S, NH or CH₂; and when R¹ represents hydroxy, amino or nitro, R², R³, R⁴ and R⁵ represent hydrogen ad R⁶ represents hydrogen, lower alkyl, alkanoyl or benzoyl groups.

19. A compound according to claim 1 wherein lower alkyl is $(C_1-C_8)$ alkyl, lower alkenyl is $(C_2-C_8)$ alkenyl and lower alkoxy is $(C_1-C_8)$ alkoxy.

20. A compound of the formula 1 having 20(S),5(S) configuration substantially free from the 20(S),5(R) stereoisomer, where R¹ through R⁶ have the meaning described in claim 1.

21. A compound of formula 1,

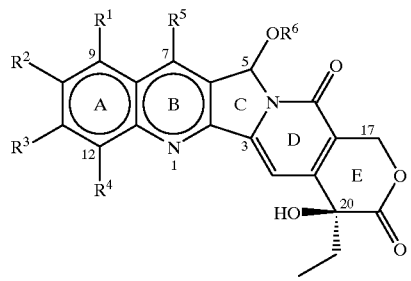

wherein R¹, R², R³, and R⁴ independently represent hydrogen or represent a group selected from hydroxy, lower alkoxy, lower alkanoyl, nitro, cyano, halo, carboxy, amino, substituted amino, where the amino group is mono or disubstituted; lower alkyl, or substituted lower alkyl; or R² and R³ together represent —O—(CH₂)ₙ—O— where n=1 or 2; each R¹, R², R³, and R⁴ are not the same except where each or R¹, R², R³, and R⁴ are hydrogen;

R⁵ represents hydrogen, lower alkyl, substituted lower alkyl, wherein the substituents are selected from hydroxy, halogen, lower alkoxy, benzyloxy, carboxy, amido, or amino where the amino group is mono or disubstituted, when the amino group is disubstituted the substituents are independent or together with the linking nitrogen atom form a saturated 5 or 6 membered heterocyclic ring of formula (A);

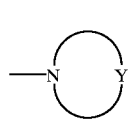

(A)

where Y represents O, S, NH or CH₂; or R⁵ represents lower aralkyl, where the aryl group is selected from phenyl, biphenyl or naphthyl; and R⁶ represents phenyl or benzyl where the phenyl group may be unsubstituted or substituted with mono, di or trisubstituents selected from halogen, lower alkoxy, cyano, nitro, lower alkyl, amino, or substituted amino, where the amino group is mono or disubstituted with lower alkyl groups; cycloalkyl or cycloalkyl lower alkyl where the cyclic ring has 3 to 7 ring atoms all of said ring atoms being carbon; lower alkyl groups substituted with saturated 5 to 7 membered heterocyclic ring of formula (B),

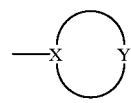

(B)

where X represents CH or N and Y represents O, S, NH or CH₂; substituted benzoyl; lower alkenyl, substituted lower alkyl or substituted lower alkenyl, wherein the substituents are selected from halogen, hydroxy, lower alkoxy, aryloxy, thio, thioalkyl, thioaryl, aryl, wherein the aryl group is selected from phenyl, biphenyl, or naphthyl; heteroaryl, carboxy, cyano, nitro, amido or amino in which the amino group can be unsubstituted or mono, or disubstituted, wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

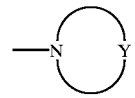

(A)

where Y represents, O, S, NH or CH₂; or

R⁶ represents substituted lower alkanoyl where the substituents are selected from halogen, lower alkoxy, aryloxy, thio, thioalkyl, thioaryl, aryl, wherein the aryl group is selected from phenyl, biphenyl, or naphthyl; heteroaryl, carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxyl, amido, amino or lower alkylamino, when the amino group is disubstituted the substituents are independent or together with the linking nitrogen atom form a saturated 5 or 6 membered heterocyclic group of formula (A),

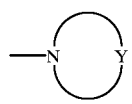

(A)

where Y represents O, S, NH or $CH_2$; and when $R^1$ represents hydroxy, amino or nitro, $R^2$, $R^3$, $R^4$ and $R^5$ represent hydrogen and $R^6$ represents hydrogen, lower alkyl, alkanoyl or benzoyl groups.

22. A compound according to claim 21 wherein when $R^1$, $R^2$, $R^3$, or $R^4$ is substituted amino the substituent is selected from lower alkyl, lower haloalkyl, benzyl, benzoyl, carboxyl, amido or lower alkylamino.

23. A compound according to claim 21 wherein when $R^1$, $R^2$, $R^3$, or $R^4$ is substituted lower alkyl the substituent is selected from hydroxyl, lower haloalkyl, benzyl, lower alkoxy, benzyloxy, cyano, nitro, amino or lower alkylamino.

24. A compound according to claim 21 wherein when $R^5$ represents substituted amino the substituent is selected from lower alkyl, lower haloalkyl, benzyl or benzoyl.

25. A compound according to claim 21 wherein when $R^6$ is benzoyl and the phenyl group is substituted, the substituents are selected from lower alkyl, lower haloalkyl, halogen, lower alkoxy, thioalkoxy, cyano, nitro, amido, amino, or lower alkylamino.

26. A compound according to claim 21 wherein the heteroaryl is selected from pyridyl, quinoline, isoquinoline, indole, pyrrole, furan, benzofuran, thiophene, thiazolidine or imidazole.

27. A compound of formula 1 having 20(S),5(S) configuration substantially free from the 20(S),5(R) stereoisomer where $R^1$ through $R^6$ have the meaning described in claim 21.

28. A compound of formula 1 having 20(S),5(R) configuration substantially free from the 20(S)5(S) stereoisomer where $R^1$ through $R^6$ have the meaning described in claim 21.

29. A pharmaceutical composition comprising an effective amount of a compound of formula 1 as defined in claim 21 or a pharmaceutically acceptable salt thereof and a pharmaceutically acceptable non-toxic excipient, diluent or solvent.

30. A method of treating leukemia, lymphoma, nonsmall cell lung cancer, cancer of the central nervous system, breast, colon, ovarian or renal cancer comprising administering to a patient in need thereof an effective amount of a compound of formula 1 as defined in claim 21 or a pharmaceutically acceptable salt thereof.

31. A process for the preparation of a compound of the formula 1,

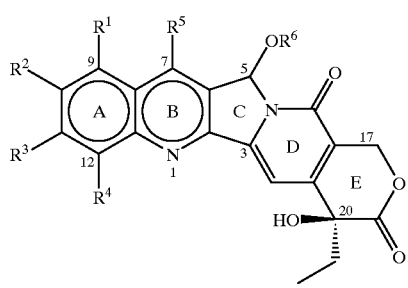

which comprises the steps of:

(i) reacting the compounds of the formula 2,

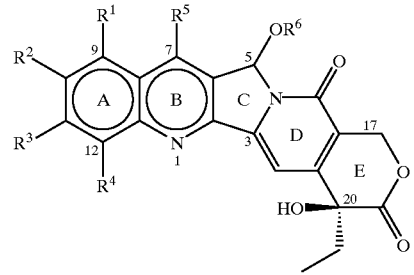

where $R^1$ to $R^5$ have the meaning described in claim 23, in the presence of an acid, said acid selected from inorganic or Lewis acids and a ferric salt, with a compound having the formula $R^6$—OH where $R^6$ represents lower alkyl, lower alkenyl, ($C_3$–$C_7$) cycloalkyl, haloalkyl or hydroxyalkyl to obtain compounds of the formula 12 and compounds of the formula 13,

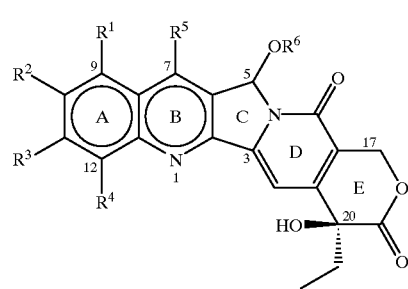

12

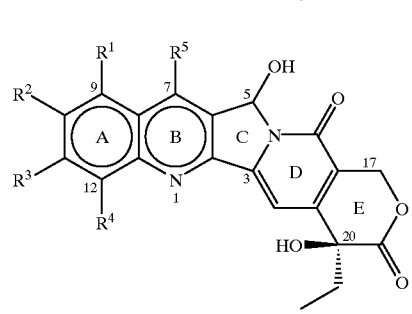

13

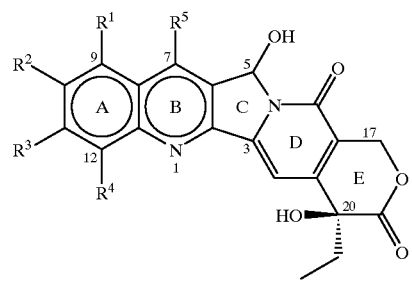

wherein $R^1$, $R^2$, $R^3$, $R^4$ and $R^5$ have the meaning described in claim 21, optionally;

(ii) separating the compounds of the formula 12 and 13 prepared in step (i), optionally;

(iii) hydrolyzing the compounds of the formula 12 to obtain additional amounts of the compounds of the formula 13, and optionally;

(iv) reacting the compound of the formula 13, in the presence of an acid, selected from inorganic acids, Lewis acids or organic acids with a compound having the formula $R^6$—OH to obtain compounds of the formula 1,

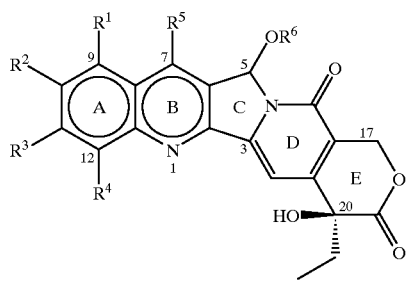

where $R^1$, $R^2$, $R^3$, $R^4$ and $R^5$ have the meaning described in claim 23 and $R^6$ represents phenyl or benzyl where the phenyl group may be unsubstituted or substituted with mono, di or trisubstituents selected from halogen, lower alkoxy, cyano, nitro, lower alkyl, amino, or substituted amino, where the amino group is mono or disubstituted with lower alkyl groups; cycloalkyl or cycloalkyl lower alkyl where the cyclic ring has 3 to 7 ring atoms all of said atoms being carbon; lower alkyl groups substituted with saturated 5 to 7 membered heterocyclic ring of formula (B),

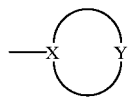

(B)

where X represents CH or N and Y represents O, S, NH or $CH_2$; substituted benzoyl; lower alkenyl, substituted lower alkyl, or substituted lower alkenyl wherein the substituents are selected from halogen, hydroxy, lower alkoxy, aryloxy, thio, thioalkyl, thioaryl, aryl, wherein the aryl group is selected from phenyl, biphenyl, or naphthyl; heteroaryl, carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

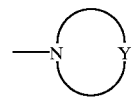

(A)

where Y represents O, S, NH or $CH_2$; or $R^6$ represents substituted lower alkanoyl wherein the substituents are selected from halogen, lower alkoxy, aryloxy, thio, thioalkyl, thioaryl, aryl, wherein the aryl group is selected from phenyl, biphenyl, or naphthyl; heteroaryl, carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

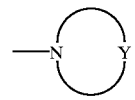

(A)

where Y represents O, S, NH or $CH_2$; and when $R^1$ represents hydroxy, amino or nitro, $R^2$, $R^3$, $R^4$ and $R^5$ represent hydrogen and $R^6$ represents hydrogen, lower alkyl, alkanoyl or benzoyl groups.

\* \* \* \* \*